(12) United States Patent
Takiguchi et al.

(10) Patent No.: US 7,078,115 B2
(45) Date of Patent: Jul. 18, 2006

(54) METAL COORDINATION COMPOUND AND ELECTROLUMINESCENCE DEVICE

(75) Inventors: Takao Takiguchi, Tokyo (JP); Akira Tsuboyama, Kanagawa-ken (JP); Shinjiro Okada, Kanagawa-ken (JP); Jun Kamatani, Kanagawa-ken (JP); Seishi Miura, Kanagawa-ken (JP); Takashi Moriyama, Kanagawa-ken (JP); Satoshi Igawa, Kanagawa-ken (JP); Manabu Furugori, Kanagawa-ken (JP); Hidemasa Mizutani, Kanagawa-ken (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 10/942,861

(22) Filed: Sep. 17, 2004

(65) Prior Publication Data

US 2005/0085654 A1    Apr. 21, 2005

Related U.S. Application Data

(62) Division of application No. 10/181,342, filed as application No. PCT/JP02/06001 on Jun. 17, 2002, now Pat. No. 6,824,894.

(30) Foreign Application Priority Data

Jun. 25, 2001    (JP) .............................. 2001/190662

(51) Int. Cl.
  H01L 51/54    (2006.01)
  H05B 33/14    (2006.01)
  C09K 11/06    (2006.01)

(52) U.S. Cl. ..................... 428/690; 428/917; 313/504; 546/4; 546/10; 549/3; 257/102; 257/103; 257/E51.044

(58) Field of Classification Search ................ 428/690, 428/917; 313/504, 506; 252/301.16; 257/40, 257/102, 103; 544/225; 546/4, 10
See application file for complete search history.

(56) References Cited

U.S. PATENT DOCUMENTS

| 6,824,894 B1 * | 11/2004 | Takiguchi et al. .......... 428/690 |
| 2001/0019782 A1 | 9/2001 | Igarashi et al. ............. 428/690 |
| 2002/0068190 A1 | 6/2002 | Tsuboyama et al. ........ 428/690 |

FOREIGN PATENT DOCUMENTS

| EP | 1191612 | 3/2002 |
| EP | 1 211 257 | 6/2002 |
| JP | 2001-181616 | 7/2001 |
| JP | 2001-181617 | 7/2001 |
| JP | 2002-105055 | 4/2002 |
| JP | 2002-175884 | 6/2002 |
| WO | 00/57676 | 9/2000 |
| WO | 01/41512 | 6/2001 |
| WO | WO 02/02714 | 1/2002 |
| WO | WO 02/15645 | 2/2002 |
| WO | 02/44189 | 6/2002 |

OTHER PUBLICATIONS

Machine-assisted translation of JP 2001-181617 (Jul. 2001).*
Thummel et al., "Preparation of 3,2'-Annelated 2-Phenylpyridines and Their Cyclopalladation Chemistry", J. Org. Chem., vol. 52, No. 1, pp. 73-78, Jan. 9, 1987.
C.H. Chen et al., "Recent Developments in Molecular Organic Electroluminescent Materials", Macromol. Symp., vol. 125, pp. 1-48 (1997), no month.
M.A. Baldo et al., "Very High-Efficiency Green Organic Light-Emitting Devices Based on Electrophosphorescence", App. Phys. Lett., vol. 75, No. 1, pp. 4-6 (Jul. 5, 1999).
D.F. O'Brien et al., "Improved Energy Transfer in Electrophosphorescent Devices", Appl. Phys., Lett., vol. 74, No. 3, pp. 442-444 (Jan. 18, 1999).
C. Cornioley-Deuschel, et al., "Complexes with a Pincers", Helv. Chim. Acta, vol. 71, No. 1, pp. 130-133 (1988), no month.
C. Deuschel-Cornioley, et al., "A New Type of 'Square Planar' Platinum(II) Complex Showing Helical Chirality", J. Chem. Soc., Chem. Commun., vol. 2, pp. 121-122 (1990), no month.
International Preliminary Examination Report dated Feb. 2. 2004 for PCT/JPO2/06001.
M. Maestri, et al., "Spectroscopic and Electrochemical Properties of Pt (II) Complexes with Aromatic Terdendate (C▲N▲C) Cyclometallating Ligands", J. Photochem. Photobiol. A: Chem., vol. 67, pp. 173-179 (1992), no month.
S. Lamansky, et al., "Synthesis and Characterization of Phosphorescent Cyclometalated Iridium Complexes", Inorg. Chem., vol. 40, pp. 1704-1711 (2001), published on Web Mar. 1, 2001.

(Continued)

Primary Examiner—Marie Yamnitzky
(74) Attorney, Agent, or Firm—Fitzpatrick, Cella, Harper & Scinto

(57) ABSTRACT

A metal coordination compound having a basic structure represented by formula: $ML_mL'_n$ (1), wherein M is a metal atom of Ir, Pt, Rh or Pd; L and L' are mutually different bidentate ligands; m is 1, 2 or 3; wherein at least one bidentate ligand has a partial structure formed by condensation via an alkylene group having 2–10 carbon atoms, is provided. In an electroluminescence device composed of one or a plurality of organic films disposed between a cathode and an anode, at least one layer is a luminescence layer which is formed by incorporating luminescence molecules constituting the metal coordination compound having a structure of the formula (1) described above as a guest material in a host material thereby to provide an electroluminescence device producing luminescence at high efficiency and stably keeping a high luminance for a long period.

2 Claims, 2 Drawing Sheets

OTHER PUBLICATIONS

S. Lamansky, et al., "Highly Phosphorescent Bis-Cyclometalated Iridium Complexes: Synthesis, Photophysical Characterization, and Use in Organic Light Emitting Diodes", J. Am. Chem. Soc., vol. 123, pp. 4304-4312 (2001), published on Web Apr. 13, 2001.

P. Jolliet, et al., "Cyclometalated Complexes of Palladium(II) and Platinum(II): cis-Configured Homoleptic and Heteroleptic Compounds with Aromatic CN Ligands", Inorg. Chem., vol. 35, pp. 4883-4888 (1996), no month.

Y. Ohsawa, et al., "Electrochemistry and Spectroscopy of Ortho-Metalated Complexes of Ir(III) and Rh(III)", J. Phys. Chem., vol. 91, pp. 1047-1054 (1987), no month.

Lamansky, et al; "Molecularly doped polymer . . . Pt (II) and Ir (III) dopants", Organic Electronics; vol. 2, pp. 53-62 (2001).

Djurovich, et al; "Ir(III) Cyclomatalated Complexes . . . Organic LEDS"; Polymer Preprints, A.C.S., vol. 41; No.1; Mar. 2000, pp. 770-771.

* cited by examiner

METAL COORDINATION COMPOUND AND ELECTROLUMINESCENCE DEVICE

CROSS-REFERENCE TO RELATED APPLICATIONS

This application is a division of application Ser. No. 10/181,342, filed on Jul. 17, 2002, now U.S. Pat. No. 6,824,894 B2, which is a national stage submission filed under 35 U.S.C. 371 of International Application No. PCT/JP02/06001 filed Jun. 17, 2002.

TECHNICAL FIELD

The present invention relates to an electroluminescence device using an organic compound, more particularly to an organic electroluminescence device (hereinafter, referred to as an "organic EL device") using a metal coordination compound as a luminescent material.

BACKGROUND ART

An applied study on an organic EL device as a luminescence device of a high-speed responsiveness and a high efficiency has been energetically conducted. Basic structures thereof are shown in FIGS. 1(a) and (b) (e.g., Macromol. Symp. 125, 1–48 (1997)).

As shown in FIG. 1, an organic EL device generally has a structure comprising a transparent electrode 14, a metal electrode 11, and a plurality of organic film layers therebetween on a transparent substrate 15.

In the device of FIG. 1(a), the organic layers comprise a luminescence layer 12 and a hole-transporting layer 13. For the transparent electrode 14, ITO, etc., having a large work function are used, for providing a good hole-injection characteristic from the transparent electrode 14 to the hole-transporting layer 13. For the metal electrode 11, a metal, such as aluminum, magnesium or an alloy of these, having a small work function is used for providing a good electron-injection characteristic to the organic layers. These electrodes have a thickness of 50–200 nm.

For the luminescence layer 12, aluminum quinolinol complexes (a representative example thereof is Alq3 shown hereinafter), etc., having an electron-transporting characteristic and luminescence characteristic are used. For the hole-transporting layer 13, biphenyldiamine derivatives (a representative example thereof is α-NPD shown hereinafter), etc., having an electron-donative characteristic are used.

The above-structured device has a rectifying characteristic, and when an electric field is applied between the metal electrode 11 as a cathode and the transparent electrode 14 as an anode, electrons are injected from the metal electrode 11 into the luminescence layer 12 and holes are injected from the transparent electrode 15. The injected holes and electrons are recombined within the luminescence layer 12 to form excitons and cause luminescence. At this time, the hole-transporting layer 13 functions as an electron-blocking layer to increase the recombination efficiency at a boundary between the luminescence layer 12 and hole-transporting layer 13, thereby increasing the luminescence efficiency.

Further, in the structure of FIG. 1(b), an electron-transporting layer 16 is disposed between the metal electrode 11 and the luminescence layer 12. By separating the luminescence and the electron and hole-transportation to provide a more effective carrier blocking structure, efficient luminescence can be performed. For the electron-transporting layer 16, an electron-transporting material, such as an oxadiazole derivative, can be used.

Luminescence used heretofore in organic EL devices generally includes two types including fluorescence and phosphorescence. In a fluorescence device, fluorescence at the time of transition of luminescence material molecule from a singlet exciton state to the ground state is produced. On the other hand, in a phosphorescence device, luminescence via a triplet exciton state is utilized.

In recent years, the phosphorescence device providing a higher luminescence yield than the fluorescence device has been studied.

Representative published literature may include:

Article 1: Improved energy transfer in electrophosphorescent device (D. F. O'Brien, et al., Applied Physics Letters, Vol. 74, No. 3, p. 422 (1999)); and Article 2: Very high-efficiency green organic light-emitting devices based on electrophosphorescence (M. A. Baldo, et al., Applied Physics Letters, Vol. 75, No. 1, p. 4 (1999)).

In these articles, a structure including 4 organic layers as shown in FIG. 1(c) has been principally used, including, from the anode side, a hole-transporting layer 13, a luminescence layer 12, an exciton diffusion-prevention layer 17 and an electron-transporting layer 16. Materials used therein include carrier-transporting materials and phosphorescent materials. Abbreviations of the respective materials are as follows.

Alq3: aluminum quinolinol complex
α-NPD: N4,N4'-di-naphthalene-1-yl-N4,N4'-diphenyl-biphenyl-4,4'-diamine
CBP: 4,4'-N,N'-dicarbazole-biphenyl
BCP: 2,9-dimethyl-4,7-diphenyl-1,10-phenanthroline
PtOEP: platinum-octaethylporphyrin complex
Ir(ppy)₃: iridium-phenylpyridine complex

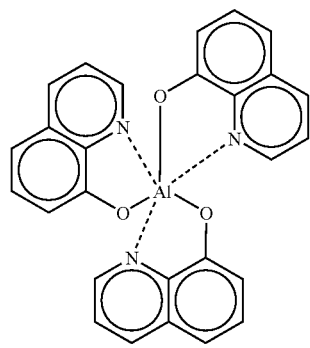

Alq3

-continued

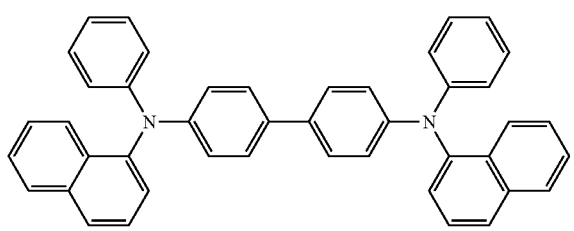
α-NPD

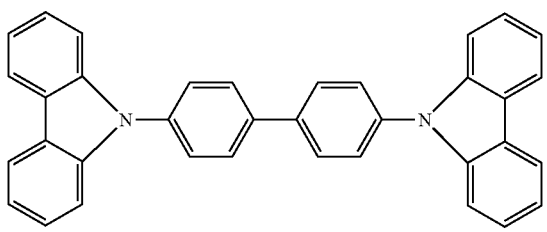
CBP

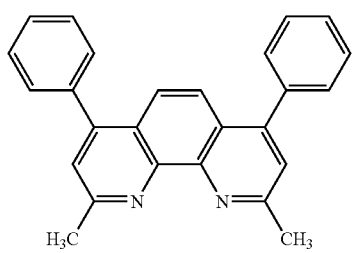
BCP

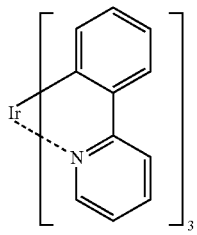
Ir(ppy)$_3$

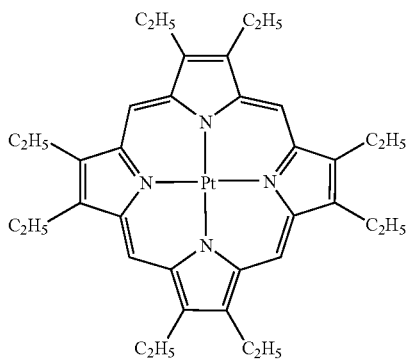
PtOEP

However, the organic EL device utilizing phosphorescence described above is accompanied with a problem regarding a deterioration in luminescence particularly in an energization state. The reason of the deterioration has not been clarified, but is conceived as follows. Generally, a life of the triplet excitons is longer by three or more digits than the life of a singlet exciton, so that excited molecules are held in a high-energy state for a longer period. As a result, it may be considered that reaction with surrounding materials such as polymer formation among the excitons, a change in minute molecular structure and a change in structure of the surrounding material are caused.

Anyway, the phosphorescence device is expected to have a high luminescence efficiency but on the other hand, the device is problematic in terms of deterioration in energized state. As a result, the luminescent material used in the phosphorescence device is desired to be a compound providing a high-efficiency luminescence and a high stability.

DISCLOSURE OF INVENTION

Accordingly, an object of the present invention is to provide a luminescence device allowing high-efficiency luminescence, retaining a high luminance or brightness for a long period and exhibiting a stability. The present invention provides a particular metal coordination compound as a novel luminescent material therefor.

A metal coordination compound according to the present invention is represented by the following formula (1):

$$ML_m L'_n \qquad (1),$$

wherein M is a metal atom of Ir, Pt, Rh or Pd; L and L' are mutually different bidentate ligands; m is 1, 2 or 3; n is 0, 1 or 2 with the proviso that m+n is 2 or 3; a partial structure ML$_m$ is represented by formula (2) shown below and a partial structure ML'$_n$ is represented by formula (3), (4) or (5) shown below:

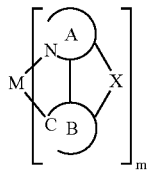
(2)

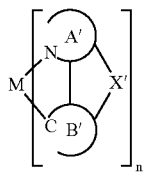
(3)

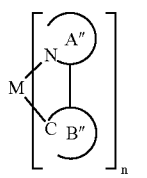
(4)

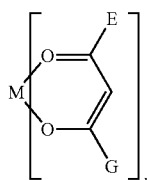
(5)

wherein N and C are nitrogen and carbon atoms, respectively; A, A' and A" are respectively a cyclic group capable of having a substituent and connected to the metal atom M via the nitrogen atom; B, B' and B" are respectively a cyclic group capable of having a substituent and connected to the metal atom M via the carbon atom;

{wherein the substituent denotes a halogen atom, a cyano group, a nitro group, a trialkylsilyl group (of which the alkyl groups are independently a linear or branched alkyl group having 1 to 8 carbon atoms), a linear or branched alkyl group having 1 to 20 carbon atoms (of which the alkyl group can include one or non-neighboring two or more methylene groups that can be replaced with —O—, —S—, —CO—, —CO—O—, —O—CO—, —CH=CH— or —C≡C— and the alkyl group can include a hydrogen atom that can be replaced with a fluorine atom), or an aromatic cyclic group capable of having a substituent (of which the substituent denotes a halogen atom, a cyano group, a nitro group, a linear or branched alkyl group having 1 to 20 carbon atoms, (of which the alkyl group can include one or non-neighboring two or more methylene groups that can be replaced with —O—, —S—, —CO—, —CO—O—, —O—CO—, —CH=CH— or —C≡C— and the alkyl group can include a hydrogen atom that can be replaced with a fluorine atom)};

A and B, A' and B', and A" and B", are respectively bonded to each other via a covalent bond; and A and B, and A' and B' are bonded to each other via X and X', respectively, in which X and X' are respectively a linear or branched alkylene group having 2–10 carbon atoms (of which the alkylene group can include one or non-neighboring two or more methylene groups that can be replaced with —O—, —S—, —CO—, —CO—O—, —O—CO—, —CH=CH— or —C≡C— and the alkylene group can include a hydrogen atom that can be replaced with a fluorine atom); and E and G are independently a linear or branched alkyl group having 1 to 20 carbon atoms (of which the alkyl group can include a hydrogen atom that can be replaced with a fluorine atom), or an aromatic cyclic group capable of having a substituent {of which the substituent denotes a halogen atom, a cyano group, a nitro group, a trialkylsilyl group (of which the alkyl groups are independently a linear or branched alkyl group having 1 to 8 carbon atoms), or a linear or branched alkyl group having 1 to 20 carbon atoms (of which the alkyl group can include one or non-neighboring two or more methylene groups that can be replaced with —O—, —S—, —CO—, —CO—O—, —O—CO—, —CH=CH— or —C≡C— and the alkyl group can include a hydrogen atom that can be replaced with a fluorine atom)}.

In the metal coordination compound according to the present invention; n in the formula (1) may preferably be 0, the partial structure ML'$_n$ in the formula (1) may preferably be represented by the formula (3), the partial structure ML'$_n$ in the formula (1) may preferably be represented by the formula (4), and the partial structure ML'$_n$ in the formula (1) may preferably be represented by the formula (5).

Further, X in the formula (1) may preferably be a linear or branched alkylene group having 2–6 carbon atoms (of which the alkylene group can include one or non-neighboring two or more methylene groups that can be replaced with —O—, —S—, —CO—, —CO—O—, —O—CO—, —CH=CH— or —C≡C— and the alkylene group can include a hydrogen atom that can be replaced with a fluorine atom).

Further, M in the formula (1) may preferably be Ir.

Further, the present invention provides an electro-luminescence device, wherein a layer comprising the above-mentioned metal coordination compound is sandwiched between opposing two electrodes between which a voltage is applied thereby to provide luminescence.

Particularly, an electroluminescence device causing phosphorescence by application of an electric field is preferred.

BEST MODE FOR PRACTICING THE INVENTION

Figure 1:
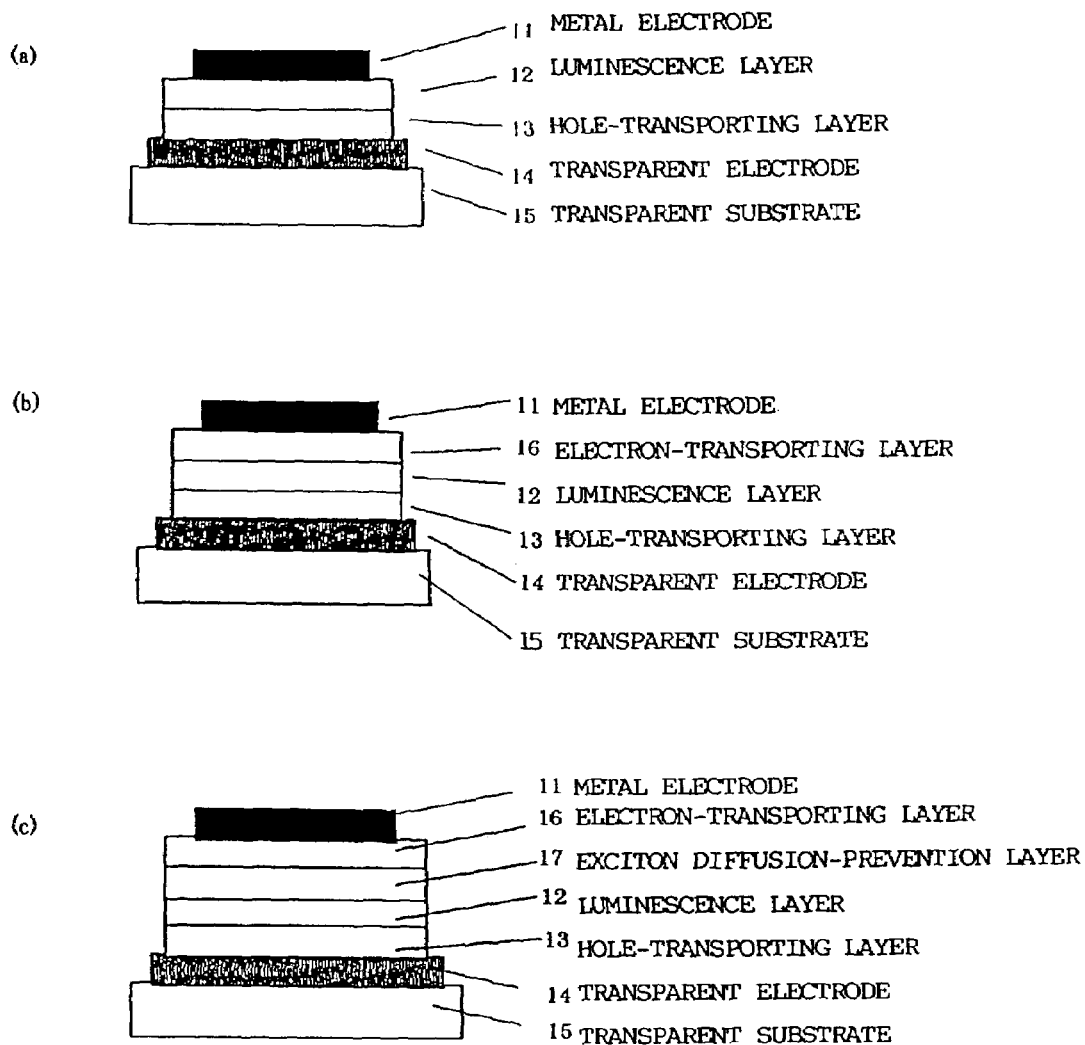
FIG. 1 illustrates embodiments of the luminescence device according to the present invention, wherein (a) is a device structure comprising 2 organic layers, (b) is a device structure comprising 3 organic layers, and (c) is a device structure comprising 4 organic layers.

Needless to say, in the case of constituting a luminescence layer with a carrier-transporting host material and a luminescent guest, the luminescent material per se requires a high quantum yield but it is important to efficiently effect energy transfer between host materials or between host and guest materials, in order to enhance a luminescence efficiency of an organic EL device. Further, the reason of a deterioration in luminescence by current application (energization) has not been clarified as yet but may be considered to be associated with at least an environmental change of the luminescent material due to the luminescence material by itself or its surrounding materials.

The present inventors have conducted various studies and have found the above-mentioned metal coordination compound of the formula (1) and also that an organic EL device using the luminescent material allows high-efficiency luminescence, keeps a high luminance (brightness) for a long period, and causes less deterioration under current application.

In the metal coordination compound represented by the above-mentioned formula (1), n may preferably be 0 or 1, more preferably 0. Further, the partial structure $ML'_n$ may preferably be represented by the above-mentioned formula (3). Further, in the formula (1) described above, X may preferably be a linear or branched alkylene group having 2–6 carbon atoms (of which the alkylene group can include one or non-neighboring two or more methylene groups that can be replaced with —O—, —S—, —CO—, —CO—O—, —O—CO—, —CH=CH— or —C≡C— and the alkylene group can include a hydrogen atom that can be replaced with a fluorine atom). Further, M in the formula may preferably be Ir or Rh, more preferably Ir.

The metal coordination compound used in the present invention emits phosphorescence, and its lowest excited state is believed to be an MLCT* (metal-to-ligand charge transfer) excited state or π-π* excited state in a triplet state. Phosphorescence is caused at the time of transition from such a state to the ground state.

By utilizing phosphorescence by photo-excitation, it is possible to determine a phosphorescence yield and a life of phosphorescence.

<Measuring Methods of Physical Properties>

Hereinbelow, measuring methods of physical properties in the present invention will be described.

(1) Discrimination Method Between Phosphorescence and Fluorescence

Discrimination of phosphorescence was effected whether a sample compound caused oxygen deactivation or not. The compound is dissolved in chloroform and divided into a solution aerated with oxygen and a solution aerated with nitrogen, followed by irradiation with light to compare their photoluminescence. As a result, luminescence resulting from the compound is little observed with respect to the oxygen-aerated solution, whereas photoluminescence can be confirmed with respect to the nitrogen-aerated solution, thus discriminating these luminescence. Hereinafter, with respect to all the compounds according to the present invention, photoluminescence is confirmed by this method unless otherwise noted specifically.

(2) A Phosphorescence Yield Used in the Present Invention may be Determined According to the Following Formula:

$$\Phi(sample)/\Phi(st)=[Sem(sample)/Iabs(sample)]/[Sem(st)/Iabs(st)],$$

wherein Iabs(st) denotes an absorption coefficient at an excitation wavelength of the standard sample; Sem(st), a luminescence spectral areal intensity when excited at the same wavelength: Iabs(sample), an absorption coefficient at an excitation wavelength of an objective compound; and Sem(sample), a luminescence spectral areal intensity when excited at the same wavelength.

Phosphorescence quantum yield values described herein are relative quantum yield with respect to a quantum yield $\Phi=1$ of $Ir(ppy)_3$ as a standard sample.

(3) Method of Measurement of Phosphorescence Life

A compound is dissolved in chloroform and spin-coated onto a quartz substrate in a thickness of ca. 0.1 μm and used as a sample for measurement. This sample is exposed to pulsative nitrogen laser light at an excitation wavelength of 337 nm at room temperature by using a luminescence life meter (made by Hamamatsu Photonics K.K.). After completion of the excitation pulses, the decay time of luminescence intensity is measured.

When an initial luminescence intensity is denoted by $I_0$, a luminescence intensity after t(sec) is defined according to the following formula with reference to a luminescence life τ(sec):

$$I=I_0 \cdot \exp(-t/\tau).$$

A phosphorescence yield of the metal coordination compound of the present invention is a high value of 0.11–0.8, and a phosphorescence life is a short one of 1–40 μsec.

If the phosphorescence life is long, the number of molecules in a triplet excited state waiting for the luminescence when used in an organic EL device is increased, thus leading to a problem of a lowering in luminescence efficiency particularly at a high current density. Accordingly, in order to enhance the luminescence efficiency, it is effective to shorten the above-mentioned phosphorescence life. The metal coordination compound of the present invention is a suitable luminescence material for an organic EL, device because of a high phosphorescence yield and a short phosphorescence life.

Further, because rotational vibration in a dihedral angle direction between the cyclic groups A and B within a molecule is suppressed by the alkylene group represented by X in the formula (2) characterizing the present invention (and further that between the cyclic groups A' and B' in a molecule is suppressed by the alkylene group shown by X' in the case where the partial structure ML'n is represented by the formula (3)), it may be considered that the metal coordination compound of the present invention is decreased in intermolecular energy deactivation pass to accomplish a high efficiency luminescence.

Further, by appropriately selecting the length of the above-mentioned alkylene groups, it becomes possible to change dihedral angles between the cyclic groups A and B and between the cyclic groups A and B and between the cyclic groups A' and B' within molecule to allow control of emission wavelength, particularly shift to shorter wavelength.

Also from the above-described viewpoint, the metal coordination compound of the present invention is suitable as a luminescent material for the organic EL device.

Further, as shown in Examples described hereinafter, it has been clarified that the metal coordination compound of the present invention exhibited an excellent performance for stability in a current conduction durability test. By a state change in intermolecular interaction due to introduction of the above-mentioned alkylene group(s) as a characteristic feature of the present invention, it is possible to control intermolecular interaction with a host material etc., thus suppressing formation of excited association product causing thermal deactivation. As a result, it may be considered that the device characteristic is improved.

<Synthesis of Iridium Coordination Compound>

Synthesis schemes of the metal coordination compound represented by the above-mentioned formula (1) used in the present invention will be shown by taking an iridium coordination compound as an example.

Synthesis of iridium coordination compound

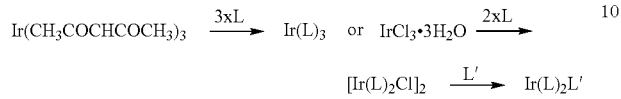

Hereinbelow, specific structural formulas of the metal coordination compound used in the present invention are shown in Tables 1—1 to 1—14, which are however only representative examples and the present invention is not restricted to these examples.

$L_1$–$L_{11}'$ used in Tables 1—1 to 1—14 have structures shown below.

$L_1$

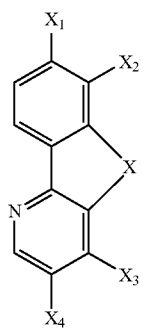

$L_2$

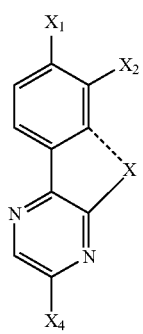

$L_3$

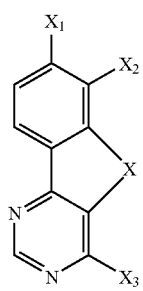

-continued $L_4$

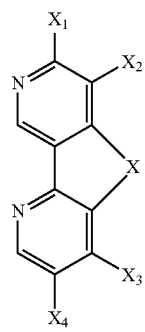

$L_5$

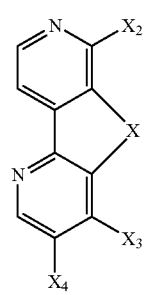

$L_6$

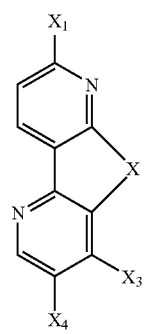

$L_7$

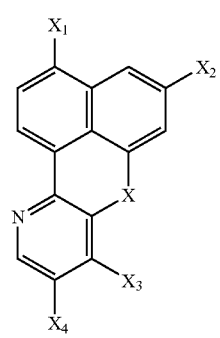

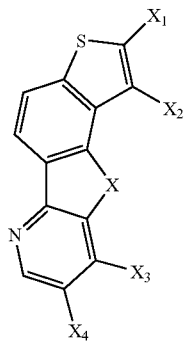
L_8
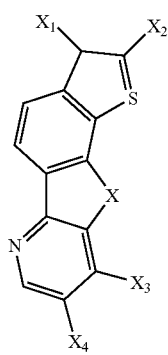
l_9
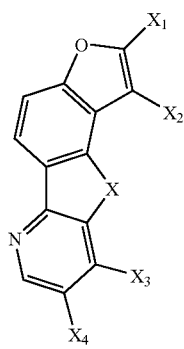
L_10
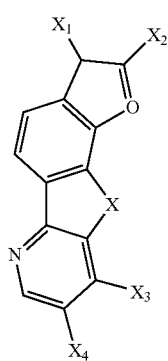
L_11
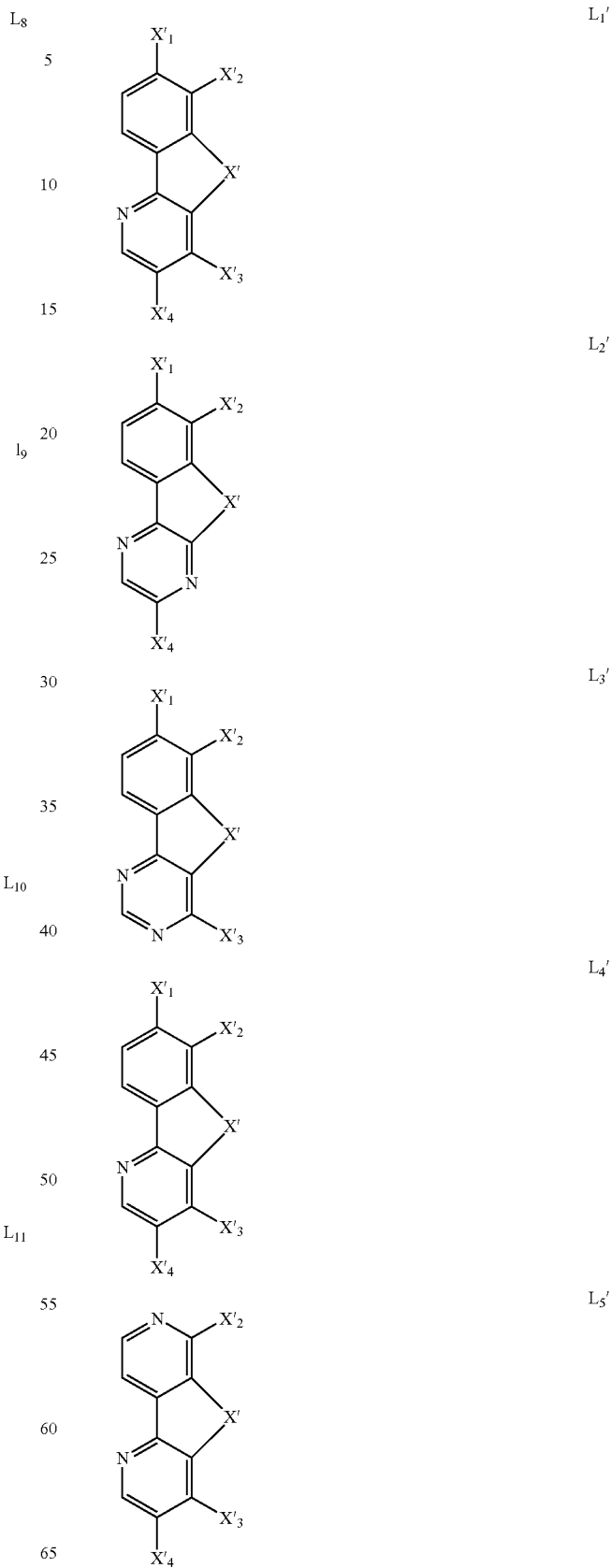

-continued
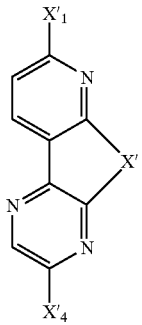
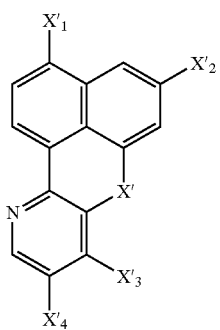
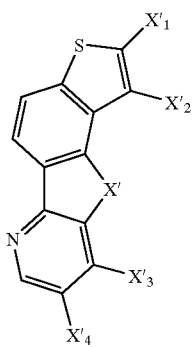
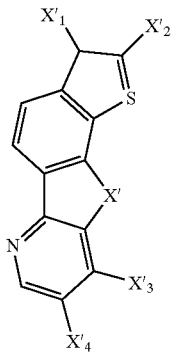
-continued
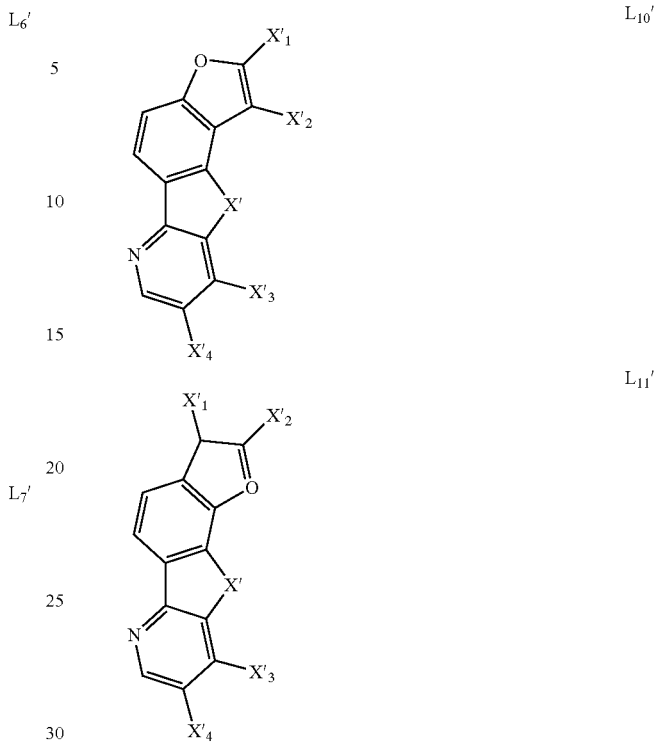
B–M' used for X and X' in Tables 1—1 to 1—14 have structures shown below.
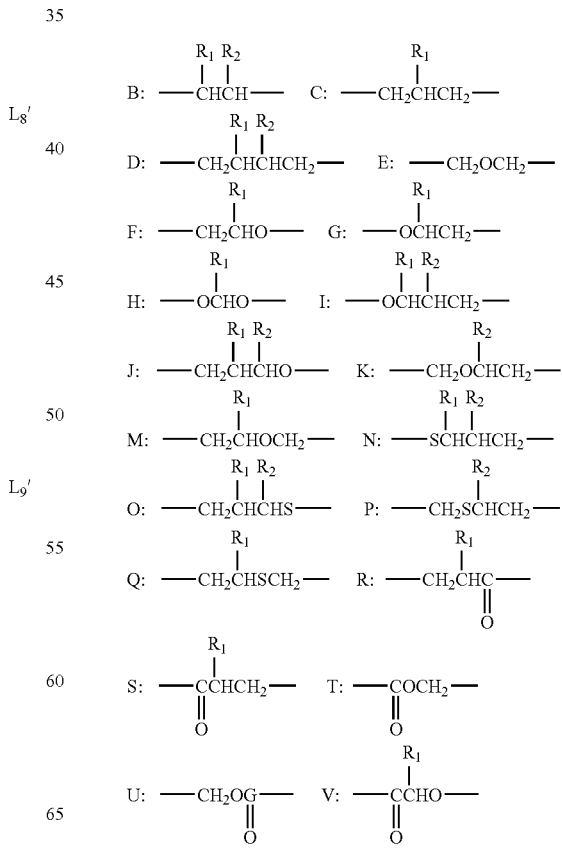

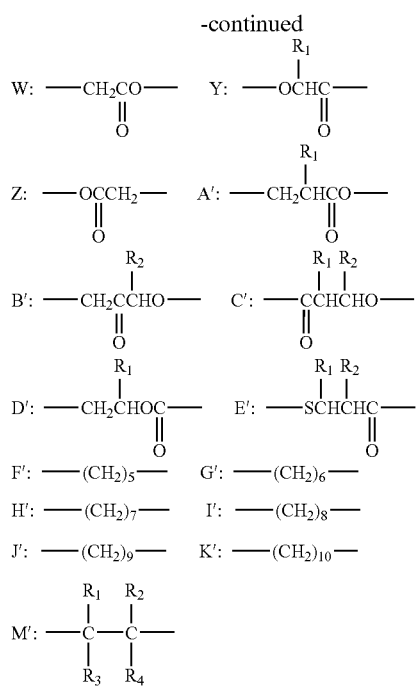
Pi–Qn2 used for A'' and B'' in Tables 1-10 and 1-11 have structures shown below.
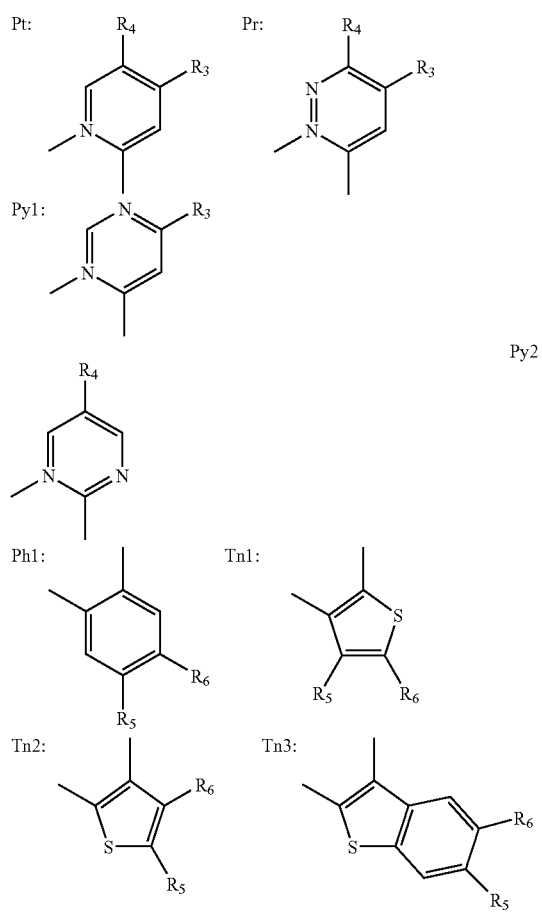
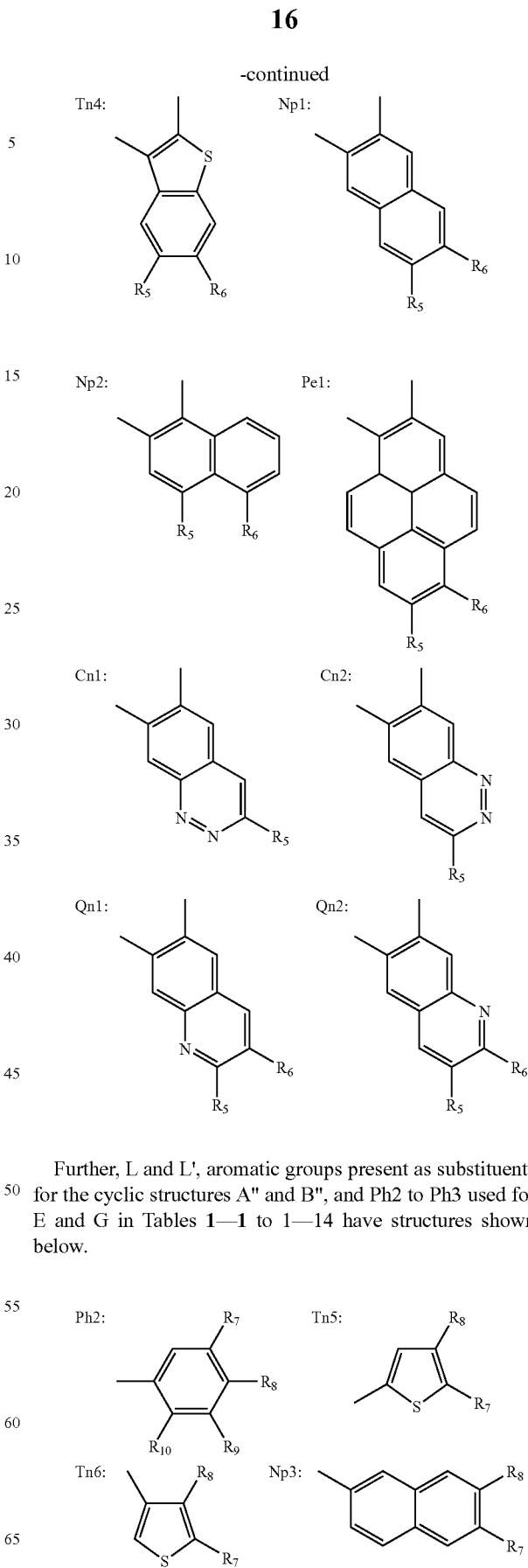
Further, L and L', aromatic groups present as substituents for the cyclic structures A'' and B'', and Ph2 to Ph3 used for E and G in Tables 1—1 to 1—14 have structures shown below.

-continued

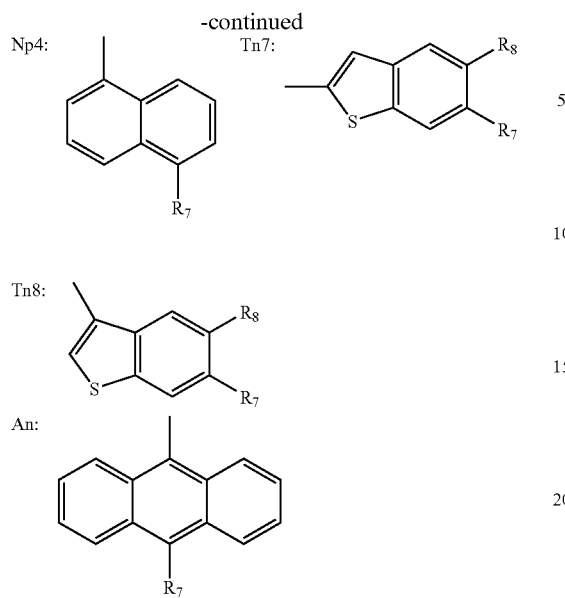
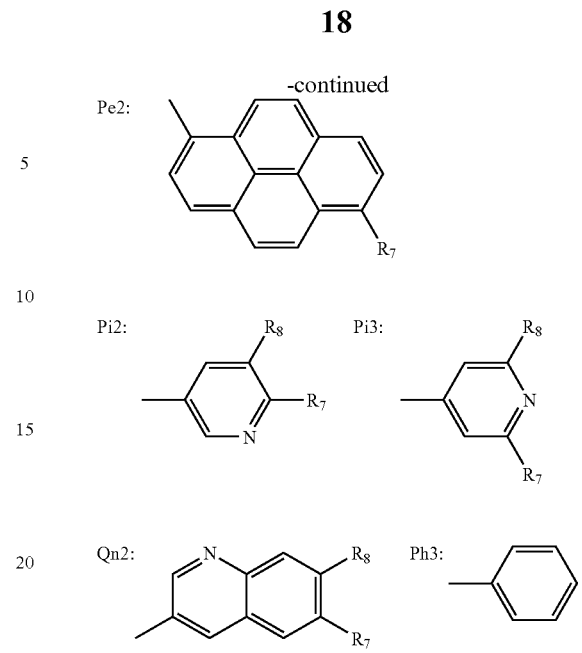

TABLE 1-1

| No | M | m | n | L | X | R1 | R2 | X1 | X2 | X3 | X4 | R7 | R8 | R9 | R10 |
|---|---|---|---|---|---|---|---|---|---|---|---|---|---|---|---|
| 1 | Ir | 3 | 0 | L1 | B | H | H | H | H | H | H | — | — | — | — |
| 2 | Ir | 3 | 0 | L1 | B | H | H | F | H | H | H | — | — | — | — |
| 3 | Ir | 3 | 0 | L1 | B | H | H | H | F | H | H | — | — | — | — |
| 4 | Ir | 3 | 0 | L1 | B | H | H | F | F | H | H | — | — | — | — |
| 5 | Ir | 3 | 0 | L1 | B | H | H | CF3 | H | H | H | — | — | — | — |
| 6 | Ir | 3 | 0 | L1 | B | H | H | H | CF3 | H | H | — | — | — | — |
| 7 | Ir | 3 | 0 | L1 | B | H | H | F | CF3 | H | H | — | — | — | — |
| 8 | Ir | 3 | 0 | L1 | B | H | H | CF3 | F | H | H | — | — | — | — |
| 9 | Ir | 3 | 0 | L1 | B | H | H | Cl | CF3 | H | H | — | — | — | — |
| 10 | Ir | 3 | 0 | L1 | B | H | H | CH3 | H | H | H | — | — | — | — |
| 11 | Ir | 3 | 0 | L1 | B | H | H | H | CH3 | H | H | — | — | — | — |
| 12 | Ir | 3 | 0 | L1 | B | H | H | OCH3 | H | H | H | — | — | — | — |
| 13 | Ir | 3 | 0 | L1 | B | H | H | H | OCH3 | H | H | — | — | — | — |
| 14 | Ir | 3 | 0 | L1 | B | H | H | OCF3 | H | H | H | — | — | — | — |
| 15 | Ir | 3 | 0 | L1 | B | H | H | H | OCF3 | H | H | — | — | — | — |
| 16 | Ir | 3 | 0 | L1 | B | H | H | Cl | H | H | H | — | — | — | — |
| 17 | Ir | 3 | 0 | L1 | B | H | H | H | Cl | H | H | — | — | — | — |
| 18 | Ir | 3 | 0 | L1 | B | H | H | Br | H | H | H | — | — | — | — |
| 19 | Ir | 3 | 0 | L1 | B | H | H | H | Br | H | H | — | — | — | — |
| 20 | Ir | 3 | 0 | L1 | B | H | H | H | OC4H9 | H | H | — | — | — | — |
| 21 | Ir | 3 | 0 | L1 | B | H | H | OC4H9 | H | H | H | — | — | — | — |
| 22 | Ir | 3 | 0 | L1 | B | H | H | H | OCH(CH3)2 | H | H | — | — | — | — |
| 23 | Ir | 3 | 0 | L1 | B | H | H | Br | H | H | H | — | — | — | — |
| 24 | Ir | 3 | 0 | L1 | B | H | H | H | H | Cl | H | — | — | — | — |
| 25 | Ir | 3 | 0 | L1 | B | H | H | H | H | H | Cl | — | — | — | — |
| 26 | Ir | 3 | 0 | L1 | B | H | H | H | H | CF3 | H | — | — | — | — |
| 27 | Ir | 3 | 0 | L1 | B | H | H | H | H | H | CF3 | — | — | — | — |
| 28 | Ir | 3 | 0 | L1 | B | H | H | Ph3 | H | H | H | — | — | — | — |
| 29 | Ir | 3 | 0 | L1 | B | H | H | Ph3 | H | H | CF3 | — | — | — | — |
| 30 | Ir | 3 | 0 | L1 | B | H | H | Ph2 | H | H | H | H | F | H | H |
| 31 | Ir | 3 | 0 | L1 | B | H | H | Ph2 | H | H | H | H | H | CF3 | H |
| 32 | Ir | 3 | 0 | L1 | B | H | H | Tn5 | H | H | H | H | H | — | — |
| 33 | Ir | 3 | 0 | L1 | B | H | H | Np3 | H | H | H | H | H | — | — |
| 34 | Ir | 3 | 0 | L1 | B | H | H | H | Tn5 | H | H | H | H | — | — |
| 35 | Ir | 3 | 0 | L1 | B | H | H | Tn7 | H | H | H | H | H | — | — |
| 36 | Ir | 3 | 0 | L1 | B | H | H | Pe2 | H | H | H | H | — | — | — |
| 37 | Ir | 3 | 0 | L1 | B | H | H | Tn8 | H | H | H | H | H | — | — |
| 38 | Ir | 3 | 0 | L1 | B | H | H | Np4 | H | H | H | H | — | — | — |
| 39 | Ir | 3 | 0 | L1 | B | H | H | Tn6 | H | H | H | H | H | — | — |
| 40 | Ir | 3 | 0 | L1 | B | CH3 | H | H | H | H | H | — | — | — | — |
| 41 | Ir | 3 | 0 | L1 | B | CH3 | H | F | H | H | H | — | — | — | — |
| 42 | Ir | 3 | 0 | L1 | B | CH3 | H | CF3 | H | H | H | — | — | — | — |
| 43 | Ir | 3 | 0 | L1 | B | CH3 | H | H | CF3 | H | H | — | — | — | — |
| 44 | Ir | 3 | 0 | L1 | B | CH3 | H | F | CF3 | H | H | — | — | — | — |
| 45 | Ir | 3 | 0 | L1 | B | H | CH3 | CF3 | F | H | H | — | — | — | — |

TABLE 1-1-continued

| No | M | m | n | L | X | R1 | R2 | X1 | X2 | X3 | X4 | R7 | R8 | R9 | R10 |
|---|---|---|---|---|---|---|---|---|---|---|---|---|---|---|---|
| 46 | Ir | 3 | 0 | L1 | B | H | CH3 | Cl | CF3 | H | H | — | — | — | — |
| 47 | Ir | 3 | 0 | L1 | B | H | CH3 | OC4H9 | H | H | H | — | — | — | — |
| 48 | Ir | 3 | 0 | L1 | B | H | CH3 | H | OCH(CH3)2 | H | H | — | — | — | — |
| 49 | Ir | 3 | 0 | L1 | B | H | CH3 | Ph2 | H | H | H | H | F | H | H |
| 50 | Ir | 3 | 0 | L1 | B | H | CH3 | Np3 | H | H | H | H | H | — | — |

TABLE 1-2

| No | M | m | n | L | X | R1 | R2 | X1 | X2 | X3 | X4 | R7 | R8 | R9 | R10 |
|---|---|---|---|---|---|---|---|---|---|---|---|---|---|---|---|
| 51 | Ir | 3 | 0 | L1 | B | H | CH3 | Tn6 | H | H | H | H | H | — | — |
| 52 | Ir | 3 | 0 | L1 | B | CH3 | CH3 | H | H | H | H | — | — | — | — |
| 53 | Ir | 3 | 0 | L1 | C | H | — | H | H | H | H | — | — | — | — |
| 54 | Ir | 3 | 0 | L1 | C | H | — | F | H | H | H | — | — | — | — |
| 55 | Ir | 3 | 0 | L1 | C | H | — | H | F | H | H | — | — | — | — |
| 56 | Ir | 3 | 0 | L1 | C | H | — | F | F | H | H | — | — | — | — |
| 57 | Ir | 3 | 0 | L1 | C | H | — | CF3 | H | H | H | — | — | — | — |
| 58 | Ir | 3 | 0 | L1 | C | H | — | H | CF3 | H | H | — | — | — | — |
| 59 | Ir | 3 | 0 | L1 | C | H | — | F | CF3 | H | H | — | — | — | — |
| 60 | Ir | 3 | 0 | L1 | C | H | — | CF3 | F | H | H | — | — | — | — |
| 61 | Ir | 3 | 0 | L1 | C | H | — | Cl | CF3 | H | H | — | — | — | — |
| 62 | Ir | 3 | 0 | L1 | C | H | — | CH3 | H | H | H | — | — | — | — |
| 63 | Ir | 3 | 0 | L1 | C | H | — | H | CH3 | H | H | — | — | — | — |
| 64 | Ir | 3 | 0 | L1 | C | H | — | OCH3 | H | H | H | — | — | — | — |
| 65 | Ir | 3 | 0 | L1 | C | H | — | H | OCH3 | H | H | — | — | — | — |
| 66 | Ir | 3 | 0 | L1 | C | H | — | OCF3 | H | H | H | — | — | — | — |
| 67 | Ir | 3 | 0 | L1 | C | H | — | H | OCF3 | H | H | — | — | — | — |
| 68 | Ir | 3 | 0 | L1 | C | H | — | Cl | H | H | H | — | — | — | — |
| 69 | Ir | 3 | 0 | L1 | C | H | — | H | Cl | H | H | — | — | — | — |
| 70 | Ir | 3 | 0 | L1 | C | H | — | Br | H | H | H | — | — | — | — |
| 71 | Ir | 3 | 0 | L1 | C | H | — | H | Br | H | H | — | — | — | — |
| 72 | Ir | 3 | 0 | L1 | C | H | — | H | OC4H9 | H | H | — | — | — | — |
| 73 | Ir | 3 | 0 | L1 | C | H | — | OC4H9 | H | H | H | — | — | — | — |
| 74 | Ir | 3 | 0 | L1 | C | H | — | H | OCH(CH3)2 | H | H | — | — | — | — |
| 75 | Ir | 3 | 0 | L1 | C | H | — | Br | H | H | H | — | — | — | — |
| 76 | Ir | 3 | 0 | L1 | C | H | — | H | H | Cl | H | — | — | — | — |
| 77 | Ir | 3 | 0 | L1 | C | H | — | H | H | H | Cl | — | — | — | — |
| 78 | Ir | 3 | 0 | L1 | C | H | — | H | H | CF3 | H | — | — | — | — |
| 79 | Ir | 3 | 0 | L1 | C | H | — | H | H | H | CF3 | — | — | — | — |
| 80 | Ir | 3 | 0 | L1 | C | H | — | Ph3 | H | H | H | — | — | — | — |
| 81 | Ir | 3 | 0 | L1 | C | H | — | Ph3 | H | H | CF3 | — | — | — | — |
| 82 | Ir | 3 | 0 | L1 | C | H | — | Ph2 | H | H | H | H | F | H | H |
| 83 | Ir | 3 | 0 | L1 | C | H | — | Ph2 | H | H | H | H | H | CF3 | H |
| 84 | Ir | 3 | 0 | L1 | C | H | — | Tn5 | H | H | H | H | H | — | — |
| 85 | Ir | 3 | 0 | L1 | C | H | — | Np3 | H | H | H | H | H | — | — |
| 86 | Ir | 3 | 0 | L1 | C | H | — | H | Tn5 | H | H | H | H | — | — |
| 87 | Ir | 3 | 0 | L1 | C | H | — | Tn7 | H | H | H | H | H | — | — |
| 88 | Ir | 3 | 0 | L1 | C | H | — | Pe2 | H | H | H | H | H | — | — |
| 89 | Ir | 3 | 0 | L1 | C | H | — | Tn8 | H | H | H | H | H | — | — |
| 90 | Ir | 3 | 0 | L1 | C | H | — | Np4 | H | H | H | H | — | — | — |
| 91 | Ir | 3 | 0 | L1 | C | H | — | Tn6 | H | H | H | H | H | — | — |
| 92 | Ir | 3 | 0 | L1 | C | CH3 | — | H | H | H | H | — | — | — | — |
| 93 | Ir | 3 | 0 | L1 | C | CH3 | — | F | H | H | H | — | — | — | — |
| 94 | Ir | 3 | 0 | L1 | C | CH3 | — | CF3 | H | H | H | — | — | — | — |
| 95 | Ir | 3 | 0 | L1 | C | CH3 | — | H | CF3 | H | H | — | — | — | — |
| 96 | Ir | 3 | 0 | L1 | C | CH3 | — | F | CF3 | H | H | — | — | — | — |
| 97 | Ir | 3 | 0 | L1 | C | CH3 | — | CF3 | F | H | H | — | — | — | — |
| 98 | Ir | 3 | 0 | L1 | C | CH3 | — | Cl | CF3 | H | H | — | — | — | — |
| 99 | Ir | 3 | 0 | L1 | C | CH3 | — | OC4H9 | H | H | H | — | — | — | — |
| 100 | Ir | 3 | 0 | L1 | C | CH3 | — | H | OCH(CH3)2 | H | H | — | — | — | — |

TABLE 1-3

| No | M | m | n | L | X | R1 | R2 | X1 | X2 | X3 | X4 | R7 | R8 | R9 | R10 |
|---|---|---|---|---|---|---|---|---|---|---|---|---|---|---|---|
| 101 | Rh | 3 | 0 | L1 | B | H | H | H | H | H | H | — | — | — | — |
| 102 | Rh | 3 | 0 | L1 | B | H | H | F | H | H | H | — | — | — | — |
| 103 | Rh | 3 | 0 | L1 | B | H | H | H | F | H | H | — | — | — | — |
| 104 | Rh | 3 | 0 | L1 | B | H | H | F | F | H | H | — | — | — | — |
| 105 | Rh | 3 | 0 | L1 | B | H | H | CF3 | H | H | H | — | — | — | — |
| 106 | Rh | 3 | 0 | L1 | B | H | H | H | CF3 | H | H | — | — | — | — |
| 107 | Rh | 3 | 0 | L1 | B | H | H | F | CF3 | H | H | — | — | — | — |

TABLE 1-3-continued

| No | M | m | n | L | X | R1 | R2 | X1 | X2 | X3 | X4 | R7 | R8 | R9 | R10 |
|---|---|---|---|---|---|---|---|---|---|---|---|---|---|---|---|
| 108 | Rh | 3 | 0 | L1 | B | H | H | CF3 | F | H | H | — | — | — | — |
| 109 | Rh | 3 | 0 | L1 | B | H | H | Cl | CF3 | H | H | — | — | — | — |
| 110 | Rh | 3 | 0 | L1 | B | H | H | CH3 | H | H | H | — | — | — | — |
| 111 | Rh | 3 | 0 | L1 | B | H | H | H | CH3 | H | H | — | — | — | — |
| 112 | Rh | 3 | 0 | L1 | B | H | H | OCH3 | H | H | H | — | — | — | — |
| 113 | Rh | 3 | 0 | L1 | B | H | H | H | OCH3 | H | H | — | — | — | — |
| 114 | Rh | 3 | 0 | L1 | B | H | H | OCF3 | H | H | H | — | — | — | — |
| 115 | Rh | 3 | 0 | L1 | B | H | H | H | OCF3 | H | H | — | — | — | — |
| 116 | Rh | 3 | 0 | L1 | B | H | H | Cl | H | H | H | — | — | — | — |
| 117 | Rh | 3 | 0 | L1 | B | H | H | H | Cl | H | H | — | — | — | — |
| 118 | Rh | 3 | 0 | L1 | B | H | H | Br | H | H | H | — | — | — | — |
| 119 | Rh | 3 | 0 | L1 | B | H | H | H | Br | H | H | — | — | — | — |
| 120 | Rh | 3 | 0 | L1 | B | H | H | H | OC4H9 | H | H | — | — | — | — |
| 121 | Rh | 3 | 0 | L1 | B | H | H | OC4H9 | H | H | H | — | — | — | — |
| 122 | Rh | 3 | 0 | L1 | B | H | H | H | OCH(CH3)2 | H | H | — | — | — | — |
| 123 | Rh | 3 | 0 | L1 | B | H | H | Br | H | H | H | — | — | — | — |
| 124 | Rh | 3 | 0 | L1 | B | H | H | H | H | Cl | H | — | — | — | — |
| 125 | Rh | 3 | 0 | L1 | B | H | H | H | H | H | Cl | — | — | — | — |
| 126 | Pt | 2 | 0 | L1 | B | H | H | H | H | CF3 | H | — | — | — | — |
| 127 | Pt | 2 | 0 | L1 | B | H | H | H | H | H | CF3 | — | — | — | — |
| 128 | Pt | 2 | 0 | L1 | B | H | H | Ph3 | H | H | H | — | — | — | — |
| 129 | Pt | 2 | 0 | L1 | B | H | H | Ph3 | H | H | CF3 | — | — | — | — |
| 130 | Pt | 2 | 0 | L1 | B | H | H | Ph2 | H | H | H | H | F | H | H |
| 131 | Pt | 2 | 0 | L1 | B | H | H | Ph2 | H | H | H | H | H | CF3 | H |
| 132 | Pt | 2 | 0 | L1 | B | H | H | Tn5 | H | H | H | H | H | — | — |
| 133 | Pt | 2 | 0 | L1 | B | H | H | Np3 | H | H | H | H | H | — | — |
| 134 | Pt | 2 | 0 | L1 | B | H | H | H | Tn5 | H | H | H | H | — | — |
| 135 | Pt | 2 | 0 | L1 | B | H | H | Tn7 | H | H | H | H | H | — | — |
| 136 | Pt | 2 | 0 | L1 | B | CH3 | H | F | H | H | H | — | — | — | — |
| 137 | Pt | 2 | 0 | L1 | B | CH3 | H | CF3 | H | H | H | — | — | — | — |
| 138 | Pt | 2 | 0 | L1 | B | CH3 | H | H | CF3 | H | H | — | — | — | — |
| 139 | Pt | 2 | 0 | L1 | B | CH3 | H | F | CF3 | H | H | — | — | — | — |
| 140 | Pt | 2 | 0 | L1 | B | CH3 | H | H | H | H | H | — | — | — | — |
| 141 | Pd | 2 | 0 | L1 | B | CH3 | H | F | H | H | H | — | — | — | — |
| 142 | Pd | 2 | 0 | L1 | B | CH3 | H | CF3 | H | H | H | — | — | — | — |
| 143 | Pd | 2 | 0 | L1 | B | CH3 | H | H | CF3 | H | H | — | — | — | — |
| 144 | Pd | 2 | 0 | L1 | B | CH3 | H | F | CF3 | H | H | — | — | — | — |
| 145 | Pd | 2 | 0 | L1 | B | H | CH3 | CF3 | F | H | H | — | — | — | — |
| 146 | Pd | 2 | 0 | L1 | B | H | CH3 | Cl | CF3 | H | H | — | — | — | — |
| 147 | Pd | 2 | 0 | L1 | B | H | CH3 | OC4H9 | H | H | H | — | — | — | — |
| 148 | Pd | 2 | 0 | L1 | B | H | CH3 | H | OCH(CH3)2 | H | H | — | — | — | — |
| 149 | Pd | 2 | 0 | L1 | B | H | CH3 | Ph2 | H | H | H | H | F | H | H |
| 150 | Pd | 2 | 0 | L1 | B | H | CH3 | Np3 | H | H | H | H | H | — | — |

TABLE 1-4

| No | M | m | n | L | X | R1 | R2 | X1 | X2 | X3 | X4 | R7 | R8 | R9 | R10 |
|---|---|---|---|---|---|---|---|---|---|---|---|---|---|---|---|
| 151 | Ir | 3 | 0 | L1 | D | H | H | H | H | H | H | — | — | — | — |
| 152 | Ir | 3 | 0 | L1 | D | H | H | F | H | H | H | — | — | — | — |
| 153 | Ir | 3 | 0 | L1 | D | H | H | H | F | H | H | — | — | — | — |
| 154 | Ir | 3 | 0 | L1 | D | H | H | F | F | H | H | — | — | — | — |
| 155 | Ir | 3 | 0 | L1 | D | H | H | CF3 | H | H | H | — | — | — | — |
| 156 | Ir | 3 | 0 | L1 | D | H | H | H | CF3 | H | H | — | — | — | — |
| 157 | Ir | 3 | 0 | L1 | D | H | H | F | CF3 | H | H | — | — | — | — |
| 158 | Ir | 3 | 0 | L1 | D | H | H | CF3 | F | H | H | — | — | — | — |
| 159 | Ir | 3 | 0 | L1 | D | H | H | Cl | CF3 | H | H | — | — | — | — |
| 160 | Ir | 3 | 0 | L1 | D | H | H | CH3 | H | H | H | — | — | — | — |
| 161 | Ir | 3 | 0 | L1 | D | H | H | H | CH3 | H | H | — | — | — | — |
| 162 | Ir | 3 | 0 | L1 | D | CH3 | H | OCH3 | H | H | H | — | — | — | — |
| 163 | Ir | 3 | 0 | L1 | D | H | CH3 | H | OCH3 | H | H | — | — | — | — |
| 164 | Ir | 3 | 0 | L1 | D | CH3 | CH3 | OCF3 | H | H | H | — | — | — | — |
| 165 | Ir | 3 | 0 | L1 | D | H | H | H | OCF3 | H | H | — | — | — | — |
| 166 | Ir | 3 | 0 | L1 | E | — | — | H | H | H | H | — | — | — | — |
| 167 | Ir | 3 | 0 | L1 | E | — | — | H | Cl | H | H | — | — | — | — |
| 168 | Ir | 3 | 0 | L1 | E | — | — | Br | H | H | H | — | — | — | — |
| 169 | Ir | 3 | 0 | L1 | E | — | — | H | Br | H | H | — | — | — | — |
| 170 | Ir | 3 | 0 | L1 | E | — | — | H | OC4H9 | H | H | — | — | — | — |
| 171 | Ir | 3 | 0 | L1 | F | H | — | H | H | H | H | — | — | — | — |
| 172 | Ir | 3 | 0 | L1 | F | H | — | H | OCH(CH3)2 | H | H | — | — | — | — |
| 173 | Ir | 3 | 0 | L1 | F | H | — | Br | H | H | H | — | — | — | — |
| 174 | Ir | 3 | 0 | L1 | F | H | — | H | H | Cl | H | — | — | — | — |
| 175 | Ir | 3 | 0 | L1 | F | C2H5 | — | H | H | H | Cl | — | — | — | — |
| 176 | Ir | 3 | 0 | L1 | G | H | — | H | H | CF3 | H | — | — | — | — |

TABLE 1-4-continued

| No | M | m | n | L | X | R1 | R2 | X1 | X2 | X3 | X4 | R7 | R8 | R9 | R10 |
|---|---|---|---|---|---|---|---|---|---|---|---|---|---|---|---|
| 177 | Ir | 3 | 0 | L1 | G | H | — | H | H | H | H | — | — | — | — |
| 178 | Ir | 3 | 0 | L1 | G | H | — | Ph3 | H | H | H | — | — | — | — |
| 179 | Ir | 3 | 0 | L1 | G | H | — | Ph3 | H | H | CF3 | — | — | — | — |
| 180 | Ir | 3 | 0 | L1 | G | H | — | H | H | H | H | — | — | — | — |
| 181 | Ir | 3 | 0 | L1 | H | H | — | Ph2 | H | H | H | H | H | CF3 | H |
| 182 | Ir | 3 | 0 | L1 | H | H | — | Tn5 | H | H | H | H | H | — | — |
| 183 | Ir | 3 | 0 | L1 | H | H | — | Np3 | H | H | H | H | H | — | — |
| 184 | Ir | 3 | 0 | L1 | H | CH3 | — | H | Tn5 | H | H | H | H | — | — |
| 185 | Ir | 3 | 0 | L1 | H | H | — | Tn7 | H | H | H | H | H | — | — |
| 186 | Ir | 3 | 0 | L1 | I | H | H | H | H | H | H | — | — | — | — |
| 187 | Ir | 3 | 0 | L1 | I | H | H | Tn8 | H | H | H | H | H | — | — |
| 188 | Ir | 3 | 0 | L1 | I | H | H | Np4 | H | H | H | H | — | — | — |
| 189 | Ir | 3 | 0 | L1 | I | H | H | Tn6 | H | H | H | H | H | — | — |
| 190 | Ir | 3 | 0 | L1 | I | CH3 | H | H | H | H | H | — | — | — | — |
| 191 | Ir | 3 | 0 | L1 | J | H | H | F | H | H | H | — | — | — | — |
| 192 | Ir | 3 | 0 | L1 | J | H | H | CF3 | H | H | H | — | — | — | — |
| 193 | Ir | 3 | 0 | L1 | J | H | H | H | CF3 | H | H | — | — | — | — |
| 194 | Ir | 3 | 0 | L1 | J | CH3 | H | F | CF3 | H | H | — | — | — | — |
| 195 | Ir | 3 | 0 | L1 | J | H | CH3 | CF3 | F | H | H | — | — | — | — |
| 196 | Ir | 3 | 0 | L1 | K | — | H | Cl | CF3 | H | H | — | — | — | — |
| 197 | Ir | 3 | 0 | L1 | K | — | H | OC4H9 | H | H | H | — | — | — | — |
| 198 | Ir | 3 | 0 | L1 | K | — | H | H | OCH(CH3)2 | H | H | — | — | — | — |
| 199 | Ir | 3 | 0 | L1 | K | — | H | Ph2 | H | H | H | H | F | H | H |
| 200 | Ir | 3 | 0 | L1 | K | — | CH3 | Np3 | H | H | H | H | H | — | — |

TABLE 1-5

| No | M | m | n | L | X | R1 | R2 | X1 | X2 | X3 | X4 | R7 | R8 | R9 | R10 |
|---|---|---|---|---|---|---|---|---|---|---|---|---|---|---|---|
| 201 | Ir | 3 | 0 | L1 | M | H | — | H | H | H | H | — | — | — | — |
| 202 | Ir | 3 | 0 | L1 | M | H | — | F | H | H | H | — | — | — | — |
| 203 | Ir | 3 | 0 | L1 | M | H | — | H | F | H | H | — | — | — | — |
| 204 | Ir | 3 | 0 | L1 | N | H | H | H | H | H | H | — | — | — | — |
| 205 | Ir | 3 | 0 | L1 | N | H | H | CF3 | H | H | H | — | — | — | — |
| 206 | Ir | 3 | 0 | L1 | N | CH3 | H | H | CF3 | H | H | — | — | — | — |
| 207 | Ir | 3 | 0 | L1 | O | H | H | F | CF3 | H | H | — | — | — | — |
| 208 | Ir | 3 | 0 | L1 | O | H | H | CF3 | F | H | H | — | — | — | — |
| 209 | Ir | 3 | 0 | L1 | O | H | H | Cl | CF3 | H | H | — | — | — | — |
| 210 | Ir | 3 | 0 | L1 | P | — | H | H | H | H | H | — | — | — | — |
| 211 | Ir | 3 | 0 | L1 | P | — | H | H | CH3 | H | H | — | — | — | — |
| 212 | Ir | 3 | 0 | L1 | P | — | H | OCH3 | H | H | H | — | — | — | — |
| 213 | Ir | 3 | 0 | L1 | Q | H | — | H | H | H | H | — | — | — | — |
| 214 | Ir | 3 | 0 | L1 | Q | H | — | OCF3 | H | H | H | — | — | — | — |
| 215 | Ir | 3 | 0 | L1 | Q | H | — | H | OCF3 | H | H | — | — | — | — |
| 216 | Ir | 3 | 0 | L1 | R | H | — | H | H | H | H | — | — | — | — |
| 217 | Ir | 3 | 0 | L1 | R | H | — | H | Cl | H | H | — | — | — | — |
| 218 | Ir | 3 | 0 | L1 | R | H | — | H | H | H | H | — | — | — | — |
| 219 | Ir | 3 | 0 | L1 | S | H | — | H | Br | H | H | — | — | — | — |
| 220 | Ir | 3 | 0 | L1 | S | H | — | H | OC4H9 | H | H | — | — | — | — |
| 221 | Ir | 3 | 0 | L1 | S | H | — | OC4H9 | H | H | H | — | — | — | — |
| 222 | Ir | 3 | 0 | L1 | T | — | — | H | H | H | H | — | — | — | — |
| 223 | Ir | 3 | 0 | L1 | T | — | — | Br | H | H | H | — | — | — | — |
| 224 | Ir | 3 | 0 | L1 | T | — | — | H | H | H | H | — | — | — | — |
| 225 | Ir | 3 | 0 | L1 | U | — | — | H | H | H | Cl | — | — | — | — |
| 226 | Ir | 3 | 0 | L1 | U | — | — | H | H | CF3 | H | — | — | — | — |
| 227 | Ir | 3 | 0 | L1 | U | — | — | H | H | H | CF3 | — | — | — | — |
| 228 | Ir | 3 | 0 | L1 | V | — | — | H | H | H | H | — | — | — | — |
| 229 | Ir | 3 | 0 | L1 | V | H | — | Ph3 | H | H | H | — | — | — | — |
| 230 | Ir | 3 | 0 | L1 | V | H | — | Ph2 | H | H | H | H | F | H | H |
| 231 | Ir | 3 | 0 | L1 | W | — | — | H | H | H | H | — | — | — | — |
| 232 | Ir | 3 | 0 | L1 | W | — | — | Tn5 | H | H | H | H | H | — | — |
| 233 | Ir | 3 | 0 | L1 | W | — | — | Np3 | H | H | H | H | H | — | — |
| 234 | Ir | 3 | 0 | L1 | Y | H | — | H | H | H | H | — | — | — | — |
| 235 | Ir | 3 | 0 | L1 | Y | H | — | Tn7 | H | H | H | H | H | — | — |
| 236 | Ir | 3 | 0 | L1 | Y | H | — | Pe2 | H | H | H | H | H | — | — |
| 237 | Ir | 3 | 0 | L1 | Z | — | — | H | H | H | H | — | — | — | — |
| 238 | Ir | 3 | 0 | L1 | Z | — | — | Np4 | H | H | H | H | — | — | — |
| 239 | Ir | 3 | 0 | L1 | Z | — | — | Tn6 | H | H | H | H | H | — | — |
| 240 | Ir | 3 | 0 | L1 | A' | H | — | H | H | H | H | — | — | — | — |
| 241 | Ir | 3 | 0 | L1 | A' | H | — | F | H | H | H | — | — | — | — |
| 242 | Ir | 3 | 0 | L1 | A' | CH3 | — | CF3 | H | H | H | — | — | — | — |
| 243 | Ir | 3 | 0 | L1 | B' | — | H | H | H | H | H | — | — | — | — |
| 244 | Ir | 3 | 0 | L1 | B' | — | H | F | CF3 | H | H | — | — | — | — |
| 245 | Ir | 3 | 0 | L1 | B' | — | CH3 | CF3 | F | H | H | — | — | — | — |

TABLE 1-5-continued

| No | M | m | n | L | X | R1 | R2 | X1 | X2 | X3 | X4 | R7 | R8 | R9 | R10 |
|---|---|---|---|---|---|---|---|---|---|---|---|---|---|---|---|
| 246 | Ir | 3 | 0 | L1 | C' | H | H | Cl | CF3 | H | H | — | — | — | — |
| 247 | Ir | 3 | 0 | L1 | C' | H | H | OC4H9 | H | H | H | — | — | — | — |
| 248 | Ir | 3 | 0 | L1 | C' | H | CH3 | H | H | H | H | — | — | — | — |
| 249 | Ir | 3 | 0 | L1 | D' | H | — | Ph2 | H | H | H | H | F | H | H |
| 250 | Ir | 3 | 0 | L1 | D' | CH3 | — | Np3 | H | H | H | H | H | — | — |

TABLE 1-6

| No | M | m | n | L | X | R1 | R2 | X1 | X2 | X3 | X4 | R7 | R8 | R9 | R10 |
|---|---|---|---|---|---|---|---|---|---|---|---|---|---|---|---|
| 251 | Ir | 3 | 0 | L1 | D' | H | H | H | H | H | H | — | — | — | — |
| 252 | Ir | 3 | 0 | L1 | E' | H | H | H | H | H | H | — | — | — | — |
| 253 | Ir | 3 | 0 | L1 | E' | H | H | H | F | H | H | — | — | — | — |
| 254 | Ir | 3 | 0 | L1 | E' | H | CH3 | F | F | H | H | — | — | — | — |
| 255 | Ir | 3 | 0 | L1 | F' | — | — | CF3 | H | H | H | — | — | — | — |
| 256 | Ir | 3 | 0 | L1 | F' | — | — | H | H | H | H | — | — | — | — |
| 257 | Ir | 3 | 0 | L1 | F' | — | — | F | CF3 | H | H | — | — | — | — |
| 258 | Ir | 3 | 0 | L1 | F' | — | — | CF3 | F | H | H | — | — | — | — |
| 259 | Ir | 3 | 0 | L1 | F' | — | — | Cl | CF3 | H | H | — | — | — | — |
| 260 | Ir | 3 | 0 | L1 | G' | — | — | H | H | H | H | — | — | — | — |
| 261 | Ir | 3 | 0 | L1 | G' | — | — | H | CH3 | H | H | — | — | — | — |
| 262 | Ir | 3 | 0 | L1 | G' | — | — | OCH3 | H | H | H | — | — | — | — |
| 263 | Ir | 3 | 0 | L1 | G' | — | — | H | OCH3 | H | H | — | — | — | — |
| 264 | Ir | 3 | 0 | L1 | G' | — | — | OCF3 | H | H | H | — | — | — | — |
| 265 | Ir | 3 | 0 | L1 | G' | — | — | H | OCF3 | H | H | — | — | — | — |
| 266 | Ir | 3 | 0 | L1 | H' | — | — | H | H | H | H | — | — | — | — |
| 267 | Ir | 3 | 0 | L1 | H' | — | — | H | Cl | H | H | — | — | — | — |
| 268 | Ir | 3 | 0 | L1 | H' | — | — | Br | H | H | H | — | — | — | — |
| 269 | Ir | 3 | 0 | L1 | H' | — | — | H | Br | H | H | — | — | — | — |
| 270 | Ir | 3 | 0 | L1 | H' | — | — | H | OC4H9 | H | H | — | — | — | — |
| 271 | Ir | 3 | 0 | L1 | I' | — | — | H | H | H | H | — | — | — | — |
| 272 | Ir | 3 | 0 | L1 | I' | — | — | H | OCH(CH3)2 | H | H | — | — | — | — |
| 273 | Ir | 3 | 0 | L1 | I' | — | — | Br | H | H | H | — | — | — | — |
| 274 | Ir | 3 | 0 | L1 | I' | — | — | H | H | Cl | H | — | — | — | — |
| 275 | Ir | 3 | 0 | L1 | I' | — | — | H | H | H | Cl | — | — | — | — |
| 276 | Ir | 3 | 0 | L1 | J' | — | — | H | H | H | H | — | — | — | — |
| 277 | Ir | 3 | 0 | L1 | J' | — | — | H | H | H | CF3 | — | — | — | — |
| 278 | Ir | 3 | 0 | L1 | J' | — | — | Ph3 | H | H | H | — | — | — | — |
| 279 | Ir | 3 | 0 | L1 | J' | — | — | Ph3 | H | H | CF3 | — | — | — | — |
| 280 | Ir | 3 | 0 | L1 | J' | — | — | Ph2 | H | H | H | H | F | H | H |
| 281 | Ir | 3 | 0 | L1 | K' | — | — | Ph2 | H | H | H | H | H | CF3 | H |
| 282 | Ir | 3 | 0 | L1 | K' | — | — | H | H | H | H | — | — | — | — |
| 283 | Ir | 3 | 0 | L1 | K' | — | — | Np3 | H | H | H | H | H | — | — |
| 284 | Ir | 3 | 0 | L1 | K' | — | — | H | Tn5 | H | H | H | H | — | — |
| 285 | Ir | 3 | 0 | L1 | K' | — | — | Tn7 | H | H | H | H | H | — | — |
| 286 | Rh | 3 | 0 | L1 | C | H | — | Pe2 | H | H | H | H | — | — | — |
| 287 | Rh | 3 | 0 | L1 | C | H | — | Tn8 | H | H | H | H | H | — | — |
| 288 | Rh | 3 | 0 | L1 | C | H | — | Np4 | H | H | H | H | — | — | — |
| 289 | Rh | 3 | 0 | L1 | I | H | H | Tn6 | H | H | H | H | H | — | — |
| 290 | Rh | 3 | 0 | L1 | D' | CH3 | — | H | H | H | H | — | — | — | — |
| 291 | Rh | 3 | 0 | L1 | F' | — | — | F | H | H | H | — | — | — | — |
| 292 | Pt | 2 | 0 | L1 | C | H | — | CF3 | H | H | H | — | — | — | — |
| 293 | Pt | 2 | 0 | L1 | O | H | H | H | CF3 | H | H | — | — | — | — |
| 294 | Pt | 2 | 0 | L1 | Z | — | — | F | CF3 | H | H | — | — | — | — |
| 295 | Pt | 2 | 0 | L1 | D' | H | — | CF3 | F | H | H | — | — | — | — |
| 296 | Pt | 2 | 0 | L1 | F' | — | — | Cl | CF3 | H | H | — | — | — | — |
| 297 | Pt | 2 | 0 | L1 | H' | — | — | OC4H9 | H | H | H | — | — | — | — |
| 298 | Pd | 2 | 0 | L1 | I' | — | — | H | OCH(CH3)2 | H | H | — | — | — | — |
| 299 | Pd | 2 | 0 | L1 | G | H | — | Ph2 | H | H | H | H | F | H | H |
| 300 | Pd | 2 | 0 | L1 | C | H | — | Np3 | H | H | H | H | H | — | — |

TABLE 1-7

| No | M | m | n | L / L' | X / X' | R1 / R1 | R2 / R2 | X1 / X1' | X2 / X2' | X3 / X3' | X4 / X4' | R7 / R7 | R8 / R8 | R9 / R9 | R10 / R10 |
|---|---|---|---|---|---|---|---|---|---|---|---|---|---|---|---|
| 301 | Ir | 2 | 1 | L1 | B | H | H | H | H | H | H | — | — | — | — |
|  |  |  |  | L1' | B | H | H | F | H | H | H | — | — | — | — |
| 302 | Ir | 2 | 1 | L1 | B | H | H | H | H | H | H | — | — | — | — |
|  |  |  |  | L1' | B | H | H | H | F | H | H | — | — | — | — |
| 303 | Ir | 2 | 1 | L1 | B | H | H | H | H | H | H | — | — | — | — |
|  |  |  |  | L1' | B | H | H | F | F | H | H | — | — | — | — |

TABLE 1-7-continued

| No | M | m | n | L L' | X X' | R1 R1 | R2 R2 | X1 X1' | X2 X2' | X3 X3' | X4 X4' | R7 R7 | R8 R8 | R9 R9 | R10 R10 |
|---|---|---|---|---|---|---|---|---|---|---|---|---|---|---|---|
| 304 | Ir | 2 | 1 | L1 | B | H | H | H | H | H | H | — | — | — | — |
|  |  |  |  | L1' | B | H | H | CF3 | H | H | H | — | — | — | — |
| 305 | Ir | 2 | 1 | L1 | B | H | H | H | H | H | H | — | — | — | — |
|  |  |  |  | L1' | B | H | H | H | CF3 | H | H | — | — | — | — |
| 306 | Ir | 2 | 1 | L1 | B | H | H | H | H | H | H | — | — | — | — |
|  |  |  |  | L1' | B | H | H | F | CF3 | H | H | — | — | — | — |
| 307 | Ir | 2 | 1 | L1 | B | H | H | H | H | H | H | — | — | — | — |
|  |  |  |  | L1' | B | H | H | Cl | CF3 | H | H | — | — | — | — |
| 308 | Ir | 2 | 1 | L1 | B | H | H | H | H | H | H | — | — | — | — |
|  |  |  |  | L1' | B | H | H | CH3 | H | H | H | — | — | — | — |
| 309 | Ir | 2 | 1 | L1 | B | H | H | H | H | H | H | — | — | — | — |
|  |  |  |  | L1' | B | H | H | OCF3 | H | H | H | — | — | — | — |
| 310 | Ir | 2 | 1 | L1 | B | H | H | H | H | H | H | — | — | — | — |
|  |  |  |  | L1' | B | H | H | H | OC4H9 | H | H | — | — | — | — |
| 311 | Ir | 2 | 1 | L1 | B | H | H | OC4H9 | H | H | H | — | — | — | — |
|  |  |  |  | L1' | B | H | H | H | OCH(CH3)2 | H | H | — | — | — | — |
| 312 | Ir | 2 | 1 | L1 | B | H | H | Br | H | H | H | — | — | — | — |
|  |  |  |  | L1' | B | H | H | H | H | Cl | H | — | — | — | — |
| 313 | Ir | 2 | 1 | L1 | B | H | H | H | H | H | Cl | — | — | — | — |
|  |  |  |  | L1' | B | H | H | H | H | CF3 | H | — | — | — | — |
| 314 | Ir | 2 | 1 | L1 | B | H | H | H | H | H | CF3 | — | — | — | — |
|  |  |  |  | L1' | B | H | H | Ph3 | H | H | H | — | — | — | — |
| 315 | Ir | 2 | 1 | L1 | B | H | H | Ph3 | H | H | CF3 | — | — | — | — |
|  |  |  |  | L1' | B | H | H | Ph2 | H | H | H | H | F | H | H |
| 316 | Ir | 2 | 1 | L1 | B | H | H | Ph2 | H | H | H | H | H | CF3 | H |
|  |  |  |  | L1' | B | H | H | Tn5 | H | H | H | H | H | — | — |
| 317 | Ir | 2 | 1 | L1 | B | H | H | Np3 | H | H | H | H | H | — | — |
|  |  |  |  | L1' | B | H | H | H | Tn5 | H | H | H | H | — | — |
| 318 | Ir | 2 | 1 | L1 | B | H | H | Tn7 | H | H | H | H | H | — | — |
|  |  |  |  | L1' | B | H | H | Pe2 | H | H | H | H | — | — | — |
| 319 | Ir | 2 | 1 | L1 | B | H | H | Tn8 | H | H | H | H | H | — | — |
|  |  |  |  | L1' | B | H | H | Np4 | H | H | H | H | — | — | — |
| 320 | Ir | 2 | 1 | L1 | B | H | H | Tn6 | H | H | H | H | H | — | — |
|  |  |  |  | L1' | B | CH3 | H | H | H | H | H | — | — | — | — |
| 321 | Ir | 2 | 1 | L1 | B | CH3 | H | F | H | H | H | — | — | — | — |
|  |  |  |  | L1' | B | CH3 | H | CF3 | H | H | H | — | — | — | — |
| 322 | Ir | 2 | 1 | L1 | B | CH3 | H | H | CF3 | H | H | — | — | — | — |
|  |  |  |  | L1' | B | CH3 | H | F | CF3 | H | H | — | — | — | — |
| 323 | Ir | 2 | 1 | L1 | B | H | CH3 | CF3 | F | H | H | — | — | — | — |
|  |  |  |  | L1' | B | H | CH3 | Cl | CF3 | H | H | — | — | — | — |
| 324 | Ir | 2 | 1 | L1 | B | H | CH3 | OC4H9 | H | H | H | — | — | — | — |
|  |  |  |  | L1' | B | H | CH3 | H | OCH(CH3)2 | H | H | — | — | — | — |
| 325 | Ir | 2 | 1 | L1 | B | H | CH3 | Ph2 | H | H | H | H | F | H | H |
|  |  |  |  | L1' | B | H | CH3 | Np3 | H | H | H | H | H | — | — |

TABLE 1-8

| No | M | m | n | L L' | X X' | R1 R1 | R2 R2 | X1 X1' | X2 X2' | X3 X3' | X4 X4' | R7 R7 | R8 R8 | R9 R9 | R10 R10 |
|---|---|---|---|---|---|---|---|---|---|---|---|---|---|---|---|
| 326 | Ir | 2 | 1 | L1 | B | H | H | H | H | H | H | — | — | — | — |
|  |  |  |  | L1' | C | H | — | H | H | H | H | — | — | — | — |
| 327 | Ir | 2 | 1 | L1 | B | H | H | H | H | H | H | — | — | — | — |
|  |  |  |  | L1' | C | H | — | F | H | H | H | — | — | — | — |
| 328 | Ir | 2 | 1 | L1 | B | H | H | H | H | H | H | — | — | — | — |
|  |  |  |  | L1' | C | H | — | F | F | H | H | — | — | — | — |
| 329 | Ir | 2 | 1 | L1 | B | H | H | H | H | H | H | — | — | — | — |
|  |  |  |  | L1' | C | H | — | F | CF3 | H | H | — | — | — | — |
| 330 | Ir | 2 | 1 | L1 | B | H | H | H | H | H | H | — | — | — | — |
|  |  |  |  | L1' | C | H | — | Cl | CF3 | H | H | — | — | — | — |
| 331 | Ir | 2 | 1 | L1 | B | H | H | H | H | H | H | — | — | — | — |
|  |  |  |  | L1' | D | CH3 | H | OCH3 | H | H | H | — | — | — | — |
| 332 | Ir | 2 | 1 | L1 | B | H | H | H | H | H | H | — | — | — | — |
|  |  |  |  | L1' | E | — | — | H | OC4H9 | H | H | — | — | — | — |
| 333 | Ir | 2 | 1 | L1 | B | H | H | H | H | H | H | — | — | — | — |
|  |  |  |  | L1' | F | C2H5 | — | H | H | H | Cl | — | — | — | — |
| 334 | Ir | 2 | 1 | L1 | B | H | H | H | H | H | H | — | — | — | — |
|  |  |  |  | L1' | G | H | — | Ph3 | H | H | CF3 | — | — | — | — |
| 335 | Ir | 2 | 1 | L1 | B | H | H | H | H | H | H | — | — | — | — |
|  |  |  |  | L1' | H | H | — | Ph2 | H | H | H | H | H | CF3 | H |
| 336 | Ir | 2 | 1 | L1 | B | H | H | OC4H9 | H | H | H | — | — | — | — |
|  |  |  |  | L1' | I | H | H | H | H | H | H | — | — | — | — |

TABLE 1-8-continued

| No | M | m | n | L<br>L' | X<br>X' | R1<br>R1 | R2<br>R2 | X1<br>X1' | X2<br>X2' | X3<br>X3' | X4<br>X4' | R7<br>R7 | R8<br>R8 | R9<br>R9 | R10<br>R10 |
|---|---|---|---|---|---|---|---|---|---|---|---|---|---|---|---|
| 337 | Ir | 2 | 1 | L1 | B | H | H | Br | H | H | H | — | — | — | — |
|  |  |  |  | L1' | J | H | H | CF3 | H | H | H | — | — | — | — |
| 338 | Ir | 2 | 1 | L1 | B | H | H | H | H | H | Cl | — | — | — | — |
|  |  |  |  | L1' | K | — | CH3 | Np3 | H | H | H | H | H | — | — |
| 339 | Ir | 2 | 1 | L1 | B | H | H | H | H | H | CF3 | — | — | — | — |
|  |  |  |  | L1' | M | H | — | H | F | H | H | — | — | — | — |
| 340 | Ir | 2 | 1 | L1 | B | H | H | Ph3 | H | H | CF3 | — | — | — | — |
|  |  |  |  | L1' | N | CH3 | H | H | CF3 | H | H | — | — | — | — |
| 341 | Ir | 2 | 1 | L1 | B | H | H | Ph2 | H | H | H | H | H | CF3 | H |
|  |  |  |  | L1' | O | H | H | Cl | CF3 | H | H | — | — | — | — |
| 342 | Ir | 2 | 1 | L1 | B | H | H | Np3 | H | H | H | H | H | — | — |
|  |  |  |  | L1' | P | — | H | OCH3 | H | H | H | — | — | — | — |
| 343 | Ir | 2 | 1 | L1 | B | H | H | Tn7 | H | H | H | H | H | — | — |
|  |  |  |  | L1' | Q | H | — | H | H | H | H | — | — | — | — |
| 344 | Ir | 2 | 1 | L1 | B | H | H | Tn8 | H | H | H | H | H | — | — |
|  |  |  |  | L1' | R | H | — | H | Cl | H | H | — | — | — | — |
| 345 | Ir | 2 | 1 | L1 | B | H | H | Tn6 | H | H | H | H | H | — | — |
|  |  |  |  | L1' | S | H | — | H | OC4H9 | H | H | — | — | — | — |
| 346 | Ir | 2 | 1 | L1 | B | CH3 | H | F | H | H | H | — | — | — | — |
|  |  |  |  | L1' | V | H | — | Ph2 | H | H | H | H | F | H | H |
| 347 | Ir | 2 | 1 | L1 | B | CH3 | H | H | CF3 | H | H | — | — | — | — |
|  |  |  |  | L1' | Y | H | — | Pe2 | H | H | H | H | — | — | — |
| 348 | Ir | 2 | 1 | L1 | B | H | CH3 | CF3 | F | H | H | — | — | — | — |
|  |  |  |  | L1' | A' | CH3 | — | CF3 | H | H | H | — | — | — | — |
| 349 | Ir | 2 | 1 | L1 | B | H | CH3 | OC4H9 | H | H | H | — | — | — | — |
|  |  |  |  | L1' | C' | H | H | Cl | CF3 | H | H | — | — | — | — |
| 350 | Ir | 2 | 1 | L1 | B | H | CH3 | Ph2 | H | H | H | H | F | H | H |
|  |  |  |  | L1' | D' | CH3 | — | Np3 | H | H | H | H | H | — | — |

TABLE 1-9

| No | M | m | n | L<br>L' | X<br>X' | R1<br>R1 | R2<br>R2 | X1<br>X1' | X2<br>X2' | X3<br>X3' | X4<br>X4' | R7<br>R7 | R8<br>R8 | R9<br>R9 | R10<br>R10 |
|---|---|---|---|---|---|---|---|---|---|---|---|---|---|---|---|
| 351 | Rh | 2 | 1 | L1 | B | H | H | H | H | H | H | — | — | — | — |
|  |  |  |  | L1' | B | H | H | F | H | H | H | — | — | — | — |
| 352 | Rh | 2 | 1 | L1 | B | H | H | H | H | H | H | — | — | — | — |
|  |  |  |  | L1' | B | H | H | H | F | H | H | — | — | — | — |
| 353 | Rh | 2 | 1 | L1 | B | H | H | H | H | H | H | — | — | — | — |
|  |  |  |  | L1' | B | H | H | F | F | H | H | — | — | — | — |
| 354 | Rh | 2 | 1 | L1 | B | H | H | H | H | H | H | — | — | — | — |
|  |  |  |  | L1' | B | H | H | CF3 | H | H | H | — | — | — | — |
| 355 | Rh | 2 | 1 | L1 | B | H | H | H | H | H | H | — | — | — | — |
|  |  |  |  | L1' | B | H | H | H | CF3 | H | H | — | — | — | — |
| 356 | Rh | 2 | 1 | L1 | B | H | H | H | H | H | H | — | — | — | — |
|  |  |  |  | L1' | B | H | H | F | CF3 | H | H | — | — | — | — |
| 357 | Rh | 2 | 1 | L1 | B | H | H | H | H | H | H | — | — | — | — |
|  |  |  |  | L1' | B | H | H | Cl | CF3 | H | H | — | — | — | — |
| 358 | Rh | 2 | 1 | L1 | B | H | H | H | H | H | H | — | — | — | — |
|  |  |  |  | L1' | B | H | H | CH3 | H | H | H | — | — | — | — |
| 359 | Rh | 2 | 1 | L1 | B | H | H | H | H | H | H | — | — | — | — |
|  |  |  |  | L1' | B | H | H | OCF3 | H | H | H | — | — | — | — |
| 360 | Rh | 2 | 1 | L1 | B | H | H | H | H | H | H | — | — | — | — |
|  |  |  |  | L1' | B | H | H | H | OC4H9 | H | H | — | — | — | — |
| 361 | Pt | 1 | 1 | L1 | B | H | H | OC4H9 | H | H | H | — | — | — | — |
|  |  |  |  | L1' | B | H | H | H | OCH(CH3)2 | H | H | — | — | — | — |
| 362 | Pt | 1 | 1 | L1 | B | H | H | Br | H | H | H | — | — | — | — |
|  |  |  |  | L1' | B | H | H | H | H | Cl | H | — | — | — | — |
| 363 | Pt | 1 | 1 | L1 | B | H | H | H | H | Cl | H | — | — | — | — |
|  |  |  |  | L1' | B | H | H | H | H | CF3 | H | — | — | — | — |
| 364 | Pt | 1 | 1 | L1 | B | H | H | H | H | H | CF3 | — | — | — | — |
|  |  |  |  | L1' | B | H | H | Ph3 | H | H | H | — | — | — | — |
| 365 | Pt | 1 | 1 | L1 | B | H | H | Ph3 | H | H | CF3 | — | — | — | — |
|  |  |  |  | L1' | B | H | H | Ph2 | H | H | H | H | F | H | H |
| 366 | Pd | 1 | 1 | L1 | B | H | H | Ph2 | H | H | H | H | H | CF3 | H |
|  |  |  |  | L1' | B | H | H | Tn5 | H | H | H | H | H | — | — |
| 367 | Pd | 1 | 1 | L1 | B | H | H | Np3 | H | H | H | H | H | — | — |
|  |  |  |  | L1' | B | H | H | H | Tn5 | H | H | H | H | — | — |
| 368 | Pd | 1 | 1 | L1 | B | H | H | Tn7 | H | H | H | H | H | — | — |
|  |  |  |  | L1' | B | H | H | Pe2 | H | H | H | H | — | — | — |
| 369 | Pd | 1 | 1 | L1 | B | H | H | Tn8 | H | H | H | H | H | — | — |
|  |  |  |  | L1' | B | H | H | Np4 | H | H | H | H | H | — | — |

TABLE 1-9-continued

| No | M | m | n | L<br>L' | X<br>X' | R1<br>R1 | R2<br>R2 | X1<br>X1' | X2<br>X2' | X3<br>X3' | X4<br>X4' | R7<br>R7 | R8<br>R8 | R9<br>R9 | R10<br>R10 |
|---|---|---|---|---|---|---|---|---|---|---|---|---|---|---|---|
| 370 | Pd | 1 | 1 | L1 | B | H | H | Tn6 | H | H | H | H | H | — | — |
|  |  |  |  | L1' | B | CH3 | H | H | H | H | H | — | — | — | — |
| 371 | Rh | 2 | 1 | L1 | B | H | H | H | H | H | H | — | — | — | — |
|  |  |  |  | L1' | C | H | — | Cl | CF3 | H | H | — | — | — | — |
| 372 | Rh | 2 | 1 | L1 | B | H | H | Ph3 | H | H | CF3 | — | — | — | — |
|  |  |  |  | L1' | N | CH3 | H | H | CF3 | H | H | — | — | — | — |
| 373 | Pt | 1 | 1 | L1 | B | H | H | Tn6 | H | H | H | H | H | — | — |
|  |  |  |  | L1' | S | H | — | H | OC4H9 | H | H | — | — | — | — |
| 374 | Pt | 1 | 1 | L1 | B | H | CH3 | OC4H9 | H | H | H | — | — | — | — |
|  |  |  |  | L1' | C' | H | H | Cl | CF3 | H | H | — | — | — | — |
| 375 | Pd | 1 | 1 | L1 | B | H | CH3 | Ph2 | H | H | H | H | F | H | H |
|  |  |  |  | L1' | D' | CH3 | — | Np3 | H | H | H | H | H | — | — |

TABLE 1-10

| No | M | m | n | L<br>L' | X<br>A" | R1<br>B" | R2 | X1<br>R3 | X2<br>R4 | X3<br>R5 | X4<br>R6 | R7 A"<br>R7 B" | R8 A"<br>R8 B" | R9 A"<br>R9 B" | R10 A"<br>R10 B" |
|---|---|---|---|---|---|---|---|---|---|---|---|---|---|---|---|
| 376 | Ir | 2 | 1 | L1 | B | H | H | H | H | H | H | — | — | — | — |
|  |  |  |  | — | Ph1 | Pi | H | H | H | H |  | — | — | — | — |
| 377 | Ir | 2 | 1 | L1 | B | H | H | F | CF3 | H | H | — | — | — | — |
|  |  |  |  | — | Ph1 | Pi | H | H | H | H |  | — | — | — | — |
| 378 | Ir | 2 | 1 | L1 | B | H | H | Cl | CF3 | H | H | — | — | — | — |
|  |  |  |  | — | Ph1 | Pi | H | H | H | H |  | — | — | — | — |
| 379 | Ir | 2 | 1 | L1 | B | H | H | H | OCF3 | H | H | — | — | — | — |
|  |  |  |  | — | Ph1 | Pi | H | H | H | H |  | — | — | — | — |
| 380 | Ir | 2 | 1 | L1 | B | H | H | OC4H9 | H | H | H | — | — | — | — |
|  |  |  |  | — | Ph1 | Pi | H | H | H | H |  | — | — | — | — |
| 381 | Ir | 2 | 1 | L1 | B | H | H | Ph2 | H | H | H | H | H | CF3 | H |
|  |  |  |  | — | Ph1 | Pi | Ph2 | H | H | H |  | H | F | H | H |
| 382 | Ir | 2 | 1 | L1 | B | H | H | Tn7 | H | H | H | H | H | — | — |
|  |  |  |  | — | Ph1 | Pi | H | H | H | H |  | — | — | — | — |
| 383 | Ir | 2 | 1 | L1 | B | H | CH3 | Ph2 | H | H | H | H | F | H | H |
|  |  |  |  | — | Tn2 | Pi | H | CH3 | H | H |  | — | — | — | — |
| 384 | Ir | 2 | 1 | L1 | B | H | CH3 | Np3 | H | H | H | H | H | — | — |
|  |  |  |  | — | Tn3 | Pi | H | H | H | H |  | — | — | — | — |
| 385 | Ir | 2 | 1 | L1 | C | H | — | H | H | H | H | — | — | — | — |
|  |  |  |  | — | Ph1 | Pi | H | H | H | H |  | — | — | — | — |
| 386 | Ir | 2 | 1 | L1 | D | H | H | CF3 | H | H | H | — | — | — | — |
|  |  |  |  | — | Np2 | Pi | H | H | H | CF3 |  | — | — | — | — |
| 387 | Ir | 2 | 1 | L1 | E | — | — | H | Cl | H | H | — | — | — | — |
|  |  |  |  | — | Pe1 | Py1 | H | — | H | H |  | — | — | — | — |
| 388 | Ir | 2 | 1 | L1 | F | H | — | H | OCH(CH3)2 | H | H | — | — | — | — |
|  |  |  |  | — | Tn1 | Pr | H | H | Ph3 | H |  | — | — | — | — |

TABLE 1-11

| No | M | m | n | L | X | R1 | R2 | X1 | X2 | X3 | X4 | R7 | R8 | R9 | R10 |
|---|---|---|---|---|---|---|---|---|---|---|---|---|---|---|---|
| | | | | L' | A" | B" | R3 | R4 | R5 | R6 | | R7 A" | R8 | R9 | R10 |
| | | | | | | | | | | | | R7 B" | R8 | R9 | R10 |
| 389 | Ir | 2 | 1 | L1 | H | H | — | Ph2 | H | H | H | H | H | CF3 | H |
| | | | | — | Ph1 | Pi | H | H | H | Tn5 | | H | H | — | — |
| 390 | Ir | 2 | 1 | L1 | H | CH3 | — | H | Tn5 | H | H | H | H | — | — |
| | | | | — | Ph1 | Pi | H | H | H | Tn8 | | H | H | — | — |
| 391 | Rh | 2 | 1 | L1 | I | H | H | Tn8 | H | H | H | H | H | — | — |
| | | | | — | Ph1 | Pi | H | H | H | H | | — | — | — | — |
| 392 | Rh | 2 | 1 | L1 | P | — | H | OCH3 | H | H | H | — | — | — | — |
| | | | | — | Ph1 | Pi | H | Ph2 | H | H | | F | F | F | F |
| 393 | Rh | 2 | 1 | L1 | V | H | — | Ph2 | H | H | H | H | F | H | H |
| | | | | — | Tn2 | Py2 | — | H | H | H | | — | — | — | — |
| 394 | Rh | 2 | 1 | L1 | D' | H | — | Ph2 | H | H | H | H | F | H | H |
| | | | | — | Tn3 | Pi | Np3 | H | CF3 | H | | H | H | — | — |
| 395 | Pt | 1 | 1 | L1 | F' | — | — | F | CF3 | H | H | — | — | — | — |
| | | | | — | Ph1 | Pi | H | H | H | H | | — | — | — | — |
| 396 | Pt | 1 | 1 | L1 | J' | — | — | Ph3 | H | H | CF3 | — | — | — | — |
| | | | | — | Tn1 | Pi | H | H | H | H | | — | — | — | — |
| 397 | Pt | 1 | 1 | L1 | C | H | — | Pe2 | H | H | H | H | — | — | — |
| | | | | — | Np2 | Pi | H | H | H | H | | — | — | — | — |
| 398 | Pd | 1 | 1 | L1 | B | H | H | H | H | H | H | — | — | — | — |
| | | | | — | Ph1 | Pi | H | H | H | H | | — | — | — | — |
| 399 | Pd | 1 | 1 | L1 | B | H | H | H | OCH(CH3)2 | H | H | — | — | — | — |
| | | | | — | Tn3 | Pi | Ph2 | H | H | CH3 | | H | C3F7 | H | H |
| 400 | Pd | 1 | 1 | L1 | C | H | — | H | H | H | H | — | — | — | — |
| | | | | — | Np1 | Pr | H | H | An | H | | — | — | — | — |
| | | | | | | | | | | | | H | — | — | — |

TABLE 1-12

| No | M | m | n | L | X | R1 | R2 | X1 | X2 | X3 | X4 | R7 | R8 | R9 | R10 |
|---|---|---|---|---|---|---|---|---|---|---|---|---|---|---|---|
| | | | | L | X | R1 | R2 | X1 | X2 | X3 | X4 | R7 E | R8 | R9 | R10 |
| | | | | E | | | | | | | | R7 G | R8 | R9 | R10 |
| | | | | G | | | | | | | | R7 | R8 | R9 | R10 |
| 401 | Ir | 2 | 1 | L1 | B | H | H | H | H | H | H | — | — | — | — |
| | | | | CH3 | | | | | | | | — | — | — | — |
| | | | | CH3 | | | | | | | | — | — | — | — |
| 402 | Ir | 2 | 1 | L1 | B | H | H | F | CF3 | H | H | — | — | — | — |
| | | | | CH3 | | | | | | | | — | — | — | — |
| | | | | CH3 | | | | | | | | — | — | — | — |
| 403 | Ir | 2 | 1 | L1 | B | H | H | Cl | CF3 | H | H | — | — | — | — |
| | | | | CH3 | | | | | | | | — | — | — | — |
| | | | | CH3 | | | | | | | | — | — | — | — |
| 404 | Ir | 2 | 1 | L1 | B | H | H | H | OCF3 | H | H | — | — | — | — |
| | | | | CF3 | | | | | | | | — | — | — | — |
| | | | | CF3 | | | | | | | | — | — | — | — |
| 405 | Ir | 2 | 1 | L1 | B | H | H | OC4H9 | H | H | H | — | — | — | — |
| | | | | CF3 | | | | | | | | — | — | — | — |
| | | | | CF3 | | | | | | | | — | — | — | — |
| 406 | Ir | 2 | 1 | L1 | B | H | H | Ph2 | H | H | H | H | H | CF3 | H |
| | | | | Ph3 | | | | | | | | — | — | — | — |
| | | | | Ph3 | | | | | | | | — | — | — | — |
| 407 | Ir | 2 | 1 | L1 | B | H | H | Tn7 | H | H | H | H | H | — | — |
| | | | | Ph2 | | | | | | | | H | C3H7 | H | H |
| | | | | Ph2 | | | | | | | | H | C3H7 | H | H |

TABLE 1-12-continued

| No | M | m | n | L | X | R1 | R2 | X1 | X2 | X3 | X4 | R7 | R8 E | R9 | R10 |
|----|---|---|---|---|---|----|----|----|----|----|----|----|------|----|-----|
|    |   |   |   |   | E |    |    |    |    |    |    | R7 | R8 G | R9 | R10 |
|    |   |   |   |   | G |    |    |    |    |    |    | R7 | R8   | R9 | R10 |
| 408 | Ir | 2 | 1 | L1 | B | H | CH3 | Ph2 | H | H | H | H | F | H | H |
|     |    |   |   |    | Tn5 |   |   |   |   |   |   | H | H | — | — |
|     |    |   |   |    | Tn5 |   |   |   |   |   |   |   |   |   |   |
| 409 | Ir | 2 | 1 | L1 | B | H | CH3 | Np3 | H | H | H | H | H | — | — |
|     |    |   |   |    | CH3 |   |   |   |   |   |   | — | — | — | — |
|     |    |   |   |    | Ph3 |   |   |   |   |   |   | — | — | — | — |
| 410 | Ir | 2 | 1 | L1 | C | H | — | H | H | H | H | — | — | — | — |
|     |    |   |   |    | Tn6 |   |   |   |   |   |   | H | H | — | — |
|     |    |   |   |    | Tn6 |   |   |   |   |   |   | H | H | — | — |
| 411 | Ir | 2 | 1 | L1 | D | H | H | CF3 | H | H | H | — | — | — | — |
|     |    |   |   |    | Np3 |   |   |   |   |   |   | CH3O | H | — | — |
|     |    |   |   |    | Np3 |   |   |   |   |   |   | CH3O | H | — | — |
| 412 | Ir | 2 | 1 | L1 | E | — | — | H | Cl | H | H | — | — | — | — |
|     |    |   |   |    | Np4 |   |   |   |   |   |   | F | — | — | — |
|     |    |   |   |    | Np4 |   |   |   |   |   |   | F | — | — | — |
| 413 | Ir | 2 | 1 | L1 | F | H | — | H | OCH(CH3)2 | H | H | — | — | — | — |
|     |    |   |   |    | Tn7 |   |   |   |   |   |   | CH3 | H | — | — |
|     |    |   |   |    | Tn7 |   |   |   |   |   |   | CH3 | H | — | — |

TABLE 1-13

| No | M | m | n | L | X | R1 | R2 | X1 | X2 | X3 | X4 | R7 | R8 E | R9 | R10 |
|----|---|---|---|---|---|----|----|----|----|----|----|----|------|----|-----|
|    |   |   |   |   | E |    |    |    |    |    |    | R7 | R8 G | R9 | R10 |
|    |   |   |   |   | G |    |    |    |    |    |    | R7 | R8   | R9 | R10 |
| 414 | Ir | 2 | 1 | L1 | H | H | — | Ph2 | H | H | H | H | H | CF3 | H |
|     |    |   |   |    | Tn8 |   |   |   |   |   |   | H | H | — | — |
|     |    |   |   |    | Tn8 |   |   |   |   |   |   | H | H | — | — |
| 415 | Ir | 2 | 1 | L1 | H | CH3 | — | H | Tn5 | H | H | H | H | — | — |
|     |    |   |   |    | Pe2 |   |   |   |   |   |   | H | — | — | — |
|     |    |   |   |    | Pe2 |   |   |   |   |   |   | H | — | — | — |
| 416 | Rh | 2 | 1 | L1 | I | H | H | Tn8 | H | H | H | H | H | — | — |
|     |    |   |   |    | CH3 |   |   |   |   |   |   | — | — | — | — |
|     |    |   |   |    | CH3 |   |   |   |   |   |   | — | — | — | — |
| 417 | Rh | 2 | 1 | L1 | P | — | H | OCH3 | H | H | H | — | — | — | — |
|     |    |   |   |    | CH3 |   |   |   |   |   |   | — | — | — | — |
|     |    |   |   |    | CH3 |   |   |   |   |   |   | — | — | — | — |
| 418 | Rh | 2 | 1 | L1 | V | H | — | Ph2 | H | H | H | H | F | H | H |
|     |    |   |   |    | CH3 |   |   |   |   |   |   | — | — | — | — |
|     |    |   |   |    | CH3 |   |   |   |   |   |   | — | — | — | — |
| 419 | Rh | 2 | 1 | L1 | D' | H | — | Ph2 | H | H | H | H | F | H | H |
|     |    |   |   |    | Ph3 |   |   |   |   |   |   | — | — | — | — |
|     |    |   |   |    | Ph3 |   |   |   |   |   |   | — | — | — | — |
| 420 | Pt | 1 | 1 | L1 | F' | — | — | F | CF3 | H | H | — | — | — | — |
|     |    |   |   |    | CH3 |   |   |   |   |   |   | — | — | — | — |
|     |    |   |   |    | CH3 |   |   |   |   |   |   | — | — | — | — |
| 421 | Pt | 1 | 1 | L1 | J' | — | — | Ph3 | H | H | CF3 | — | — | — | — |
|     |    |   |   |    | CF3 |   |   |   |   |   |   | — | — | — | — |
|     |    |   |   |    | CF3 |   |   |   |   |   |   | — | — | — | — |
| 422 | Pt | 1 | 1 | L1 | C | H | — | Pe2 | H | H | H | H | — | — | — |
|     |    |   |   |    | Pi2 |   |   |   |   |   |   | H | H | — | — |
|     |    |   |   |    | Pi2 |   |   |   |   |   |   | H | H | — | — |
| 423 | Pd | 1 | 1 | L1 | B | H | H | H | H | H | H | — | — | — | — |
|     |    |   |   |    | CH3 |   |   |   |   |   |   | — | — | — | — |
|     |    |   |   |    | CH3 |   |   |   |   |   |   | — | — | — | — |
| 424 | Pd | 1 | 1 | L1 | B | H | H | H | OCH9CH3)2 | H | H | — | — | — | — |
|     |    |   |   |    | CF3 |   |   |   |   |   |   | — | — | — | — |
|     |    |   |   |    | CF3 |   |   |   |   |   |   | — | — | — | — |
| 425 | Pd | 1 | 1 | L1 | C | H | — | H | H | H | H | — | — | — | — |
|     |    |   |   |    | Qn2 |   |   |   |   |   |   | H | H | — | — |
|     |    |   |   |    | Qn2 |   |   |   |   |   |   | H | H | — | — |

TABLE 1-14

| No | M | m | n | L | X | R1 | R2 | R3 | R4 | X1 | X2 | X3 | X4 |
|---|---|---|---|---|---|---|---|---|---|---|---|---|---|
| 426 | Ir | 3 | 0 | L2 | B | H | H | — | — | H | H | — | H |
| 427 | Ir | 3 | 0 | L3 | B | H | H | — | — | F | H | H | — |
| 428 | Ir | 3 | 0 | L4 | B | H | H | — | — | H | F | H | H |
| 429 | Ir | 3 | 0 | L5 | B | H | H | — | — | — | F | H | H |
| 430 | Ir | 3 | 0 | L6 | B | H | H | — | — | CF3 | — | — | H |
| 431 | Ir | 3 | 0 | L7 | B | H | H | — | — | H | H | H | H |
| 432 | Ir | 3 | 0 | L8 | B | H | H | — | — | F | CF3 | H | H |
| 433 | Ir | 3 | 0 | L9 | B | H | H | — | — | H | H | CF3 | F |
| 434 | Ir | 3 | 0 | L10 | B | H | H | — | — | H | H | H | H |
| 435 | Ir | 3 | 0 | L11 | B | H | H | — | — | H | H | H | H |
| 436 | Ir | 3 | 0 | L2' | B | H | H | — | — | H | CH3 | — | H |
| 437 | Ir | 3 | 0 | L3' | B | H | H | — | — | OCH3 | H | H | — |
| 438 | Ir | 3 | 0 | L4' | B | H | H | — | — | H | H | H | H |
| 439 | Ir | 3 | 0 | L5' | B | H | H | — | — | — | H | H | H |
| 440 | Ir | 3 | 0 | L6' | B | H | H | — | — | H | — | — | H |
| 441 | Ir | 3 | 0 | L7' | B | H | H | — | — | H | H | H | H |
| 442 | Ir | 3 | 0 | L8' | B | H | H | — | — | H | H | H | H |
| 443 | Ir | 3 | 0 | L9' | B | H | H | — | — | H | H | H | H |
| 444 | Ir | 3 | 0 | L10' | B | H | H | — | — | H | H | H | H |
| 445 | Ir | 3 | 0 | L11' | B | H | H | — | — | H | H | H | H |
| 446 | Ir | 3 | 0 | L1 | M' | CH3 | CH3 | CH3 | CH3 | H | H | H | H |
| 447 | Ir | 3 | 0 | L1 | M' | C2H5 | C2H5 | C2H5 | C2H5 | H | H | H | H |
| 448 | Ir | 3 | 0 | L1 | M' | CH3 | CH3 | CH3 | CH3 | F | H | H | H |
| 449 | Ir | 3 | 0 | L1 | M' | CH3 | CH3 | CH3 | CH3 | H | F | H | H |
| 450 | Ir | 3 | 0 | L1 | M' | CH3 | CH3 | CH3 | CH3 | F | CH3 | H | H |

Hereinbelow, the present invention will be described specifically based on Examples.

EXAMPLE 1

Synthesis of Example Compound No. 1

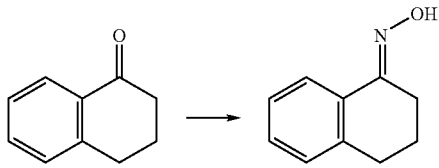

In a 2 L (liter)-three-necked flask, 69.0 g (472 mM) of α-tetralone, 50.0 g (720 mM) of hydroxylamine hydrochloride, 500 ml of ethanol and 360 ml of 2N-sodium hydroxide aqueous solution were placed and stirred for 1 hour at room temperature. The solvent was removed under reduced pressure to provide a dry solid (residue). To the residue, 500 ml of water was added and extracted three times with 150 ml of ethyl acetate. The organic layer was dried with anhydrous magnesium sulfate, followed by removal of the solvent under reduced pressure to obtain 74 g (Yield: 97.2%) of a pale yellow crystal of α-tetralone=oxime.

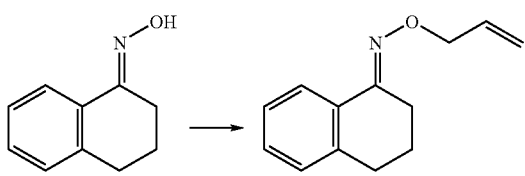

In a 1 L-three-necked flask, 80 ml of tetrahydrofuran and 23.8 g (595 M) of 60%-oily sodium hydride were placed and stirred for 5 minutes at room temperature, followed by addition thereof dropwise to solution of 74.0 g (459 mM) of α-tetralone=oxime in 500 ml of anhydrous DMF (dimethylformamide) in 15 minutes. Thereafter, the system was stirred for 1 hour at room temperature, followed by addition of 113.5 g (939 mM) of allyl bromide and further stirring for 12 hours at room temperature. After the reaction, the reaction product was subjected to removal of the solvent under reduced pressure to obtain a residue. To the residue, 500 ml of water was added and extracted three times with 200 ml of ethyl acetate. The organic layer was dried with anhydrous magnesium sulfate and subjected to removal of the solvent under reduced pressure to obtain a brown liquid. The liquid was subjected to distilling-off of the solvent under reduced pressure to obtain 79.5 g (Yield: 86.0%) of α-tetralone=oxime=O-allyl=ether having a boiling agent of 75–80° C. (6.7 Pa).

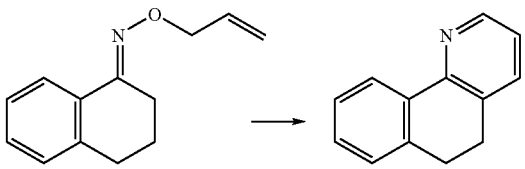

In a 1 L-autoclave, 58.0 g (288 mM) of α-tetralone=oxime=O-allyl=ether was placed and aerated with oxygen gas, followed by hermetic sealing with a cap and vigorous stirring for 5 days at 190° C. The reaction mixture was cooled to room temperature to provide a high-viscous brown liquid, which was dissolved in chloroform and extracted three times with 300 ml of 5%-hydrochloric acid. The aqueous layer was alkalified with 48%-sodium hydroxide and extracted three times with 350 ml of chloroform. The organic layer was dried with anhydrous magnesium sulfate and concentrated under reduced pressure, followed by purification by silica gel column chromatography using chloroform as an eluent and purification by silica gel column chromatography using a mixture solvent of hexane/ethyl acetate=5/1 as an eluent to obtain 7.7 g of a pale brown liquid. The liquid was purified by using a Kugelrohr distillation apparatus (ball-tube oven) to obtain 6.6 g (Yield: 12.6%) of colorless benzo[h]-5,6-dihydroquinoline.

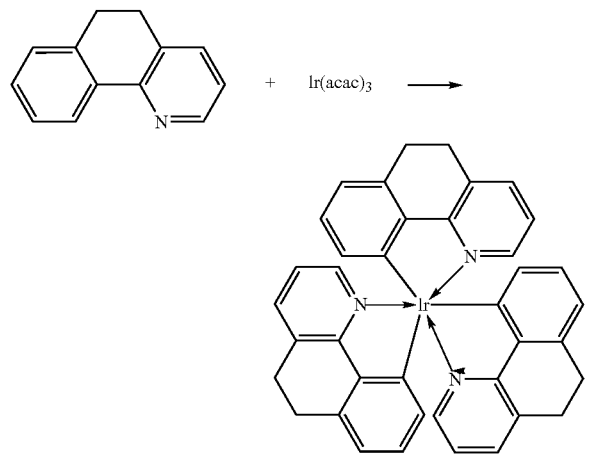

In a 100 ml-four-necked flask, 50 ml of glycerol was placed and heated for 2 hours at 130–140° C. under stirring and bubbling with nitrogen. The glycerol was cooled to 100° C. by standing, and 0.91 g (5.02 mM) of benzo[h]-5,6-dihydroquinoline and 0.50 g (1.02 mM) of iridium (III) acetylacetonate were added thereto, followed by stirring for 5 hours at 190–215° C. under heating and nitrogen stream. The reaction product was cooled to room temperature and poured into 300 ml of 1N-hydrochloric acid to obtain a precipitate, which was recovered by filtration and washed with water, followed by dissolution in acetone to remove an insoluble matter by filtration. The acetone was removed under reduced pressure to obtain a residue, which was purified by silica gel column chromatography using chloroform as an eluent to obtain 0.11 g (Yield: 14.7%) of yellow powder of iridium (III) tris{benzo[h]-5,6-dihydroquinoline}.

This compound exhibited a PL (photoluminescence) spectrum having λmax (maximum emission wavelength) of 511 nm and a quantum yield of 0.51 in a solution state. For comparison, when a solution of Ir(ppy)$_3$ as the above-mentioned conventional luminescent material which was not crosslinked with an alkylene group, different from the metal coordination compound of the present invention, was subjected to measurement of PL spectrum in a similar manner, λmax (maximum emission wavelength) was 510 nm and a quantum yield was 0.40. Further, an organic EL device prepared in Example 3 described hereinafter caused luminescence at a high luminance under application of an electric field. Further, EL spectrum thereof had a λmax (maximum emission wavelength) of 510 nm.

EXAMPLE 2

Synthesis of Ex. Comp. No. 53

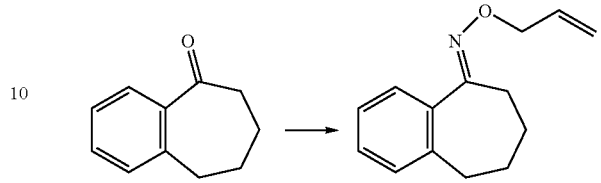

In a 3 L (liter)-three-necked flask, 166.0 g (1036 mM) of 1-benzosuberone, 125.0 g (1141 mM) of O-allylhydroxylamine hydrochloride, 93.5 g (1140 mM) of sodium acetate, 158.0 g (1143 mM) of potassium carbonate and 1500 ml of ethanol were placed and stirred for 1.5 hours at 80° C. under heating. The reaction product was cooled to room temperature and subjected to removal of the solvent under reduced pressure to obtain a residue. To the residue, 1500 ml of water was added and extracted three times with 500 ml of ethyl acetate. The organic layer was dried with anhydrous magnesium sulfate and subjected to removal of the solvent under reduced pressure to obtain a pale brown liquid. The liquid was subjected to distilling-off of the solvent under reduced pressure to obtain 221.8 g (Yield: 99.0%) of 1-benzosuberone=oxime=O-allyl=ether having a boiling agent of 75–83° C. (4.0 Pa).

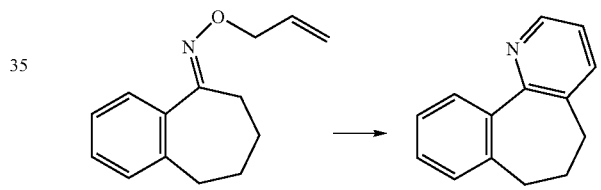

In a 5 L-autoclave, 222.0 g (1022 mM) of 1-benzosuberone=oxime=O-allyl=ether was placed and aerated with oxygen gas, followed by hermetic sealing with a cap and vigorous stirring for 3 days at 190° C. The reaction mixture was cooled to room temperature to provide a high-viscous brown liquid, which was dissolved in 2 liters of chloroform and extracted three times with 500 ml of 5%-hydrochloric acid. The aqueous layer was alkalified with 48%-sodium hydroxide and extracted three times with 500 ml of chloroform. The organic layer was dried with anhydrous magnesium sulfate and subjected to removal of the solvent under reduced pressure, followed by purification by silica gel column chromatography using a mixture solvent of hexane/ethyl acetate=5/1 as an eluent to obtain 19 g of a pale brown liquid. The liquid was purified by using a Kugelrohr distillation apparatus (ball-tube oven) to obtain 13.5 g (Yield: 6.8%) of pale green 3,2'-trimethylene-2-phenylpyridine.

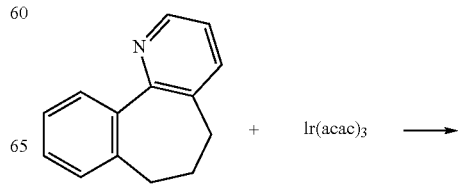

-continued

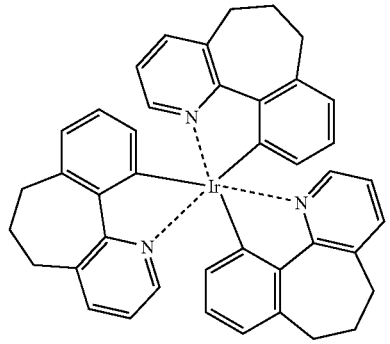

In a 100 ml-four-necked flask, 50 ml of glycerol was placed and heated for 2 hours at 130–140° C. under stirring and bubbling with nitrogen. The glycerol was cooled to 100° C. by standing, and 0.98 g (5.02 mM) of 3,2'-trimethylene-2-phenylpyridine and 0.50 g (1.02 mM) of iridium (III) acetylacetonate were added thereto, followed by stirring for 8 hours at 190–210° C. under heating and nitrogen stream. The reaction product was cooled to room temperature and poured into 300 ml of 1N-hydrochloric acid to obtain a precipitate, which was recovered by filtration and washed with water, followed by dissolution in acetone to remove an insoluble matter by filtration. The acetone was removed under reduced pressure to obtain a residue, which was purified by silica gel column chromatography using chloroform as an eluent to obtain 0.18 g (Yield: 22.7%) of yellow powder of iridium (III) tris{3,2'-trimethylene-2-phenylpyridine}. An organic EL device prepared in Example 6 described hereinafter caused bluish green luminescence under application of an electric field.

EXAMPLES 3–11 AND COMPARATIVE EXAMPLE 1

As each device structure, a device having three-layered organic layers shown in FIG. 1(b) was used.

On a glass substrate (transparent substrate 15), a 100 nm-thick ITO (transparent electrode 14) was formed and then patterned. On the ITO electrode, the following organic layers and electrode layers were successively formed in the following film thicknesses in a vacuum chamber at a vacuum of $10^{-4}$ Pa by resistance heating vacuum deposition.

Organic layer 1 (hole-transporting layer 13) (40 nm): α-NPD
Organic layer 2 (luminescence layer 12) (30 nm): CBP/luminescent material (=95/5)

This layer was formed by co-deposition of CBP as a host material with a metal coordination compound shown in Table 2 appearing hereinafter in a weight proportion of 5 wt. % as a luminescent material.

Organic layer 3 (electron-transporting layer 16) (30 nm): Alq 3
Metal electrode 1 (15 nm): AlLi alloy (Li content: 1.8 wt. %)
Metal electrode 2 (100 nm): Al After the electrode materials were formed into films, the electrodes were patterned to have an opposing electrode area of 3 mm².

Each device was supplied with an electric field with the ITO side as the anode and the Al side as the cathode by applying a voltage so that a current value became constant, thus measuring a change in luminance with time. A current amount (density) was set to 70 mA/cm² and respective devices showed luminances obtained at an initial stage in a range of 80–250 cd/m². Times required for ½ of these luminances, respectively, were evaluated as a luminance half-life (half-time).

For measurement, in order to remove factors for device deterioration due to oxygen or water, the above measurement was performed in a dry nitrogen flow after taking the device out of the vacuum chamber.

In Comparative Example 1, Ir(ppy)₃ described in the above-mentioned article 2 was used as a conventional luminescent material.

The results of current-conduction durability test for the devices using the respective compounds are shown in Table 2. The devices (of the present invention) exhibited clearly larger luminance half-life values than the device using the conventional luminescent material, thus resulting in devices with high durability resulting from a stability of a material used in the present invention.

TABLE 2

|  | Luminescence material No. | Luminance half-life (Hr) |
| --- | --- | --- |
| Example 3 | (1) | 950 |
| Example 4 | (7) | 850 |
| Example 5 | (48) | 700 |
| Example 6 | (53) | 900 |
| Example 7 | (102) | 600 |
| Example 8 | (131) | 500 |
| Example 9 | (302) | 800 |
| Example 10 | (376) | 750 |
| Example 11 | (401) | 650 |
| Comparative Example 1 | Ir(ppy)₃ | 350 |

EXAMPLE 12

An embodiment of the electroluminescence device of the present invention applied to an active-matrix type color organic EL display using a TFT circuit shown in FIG. 3 will be described with reference to FIG. 2.

Figure 2:
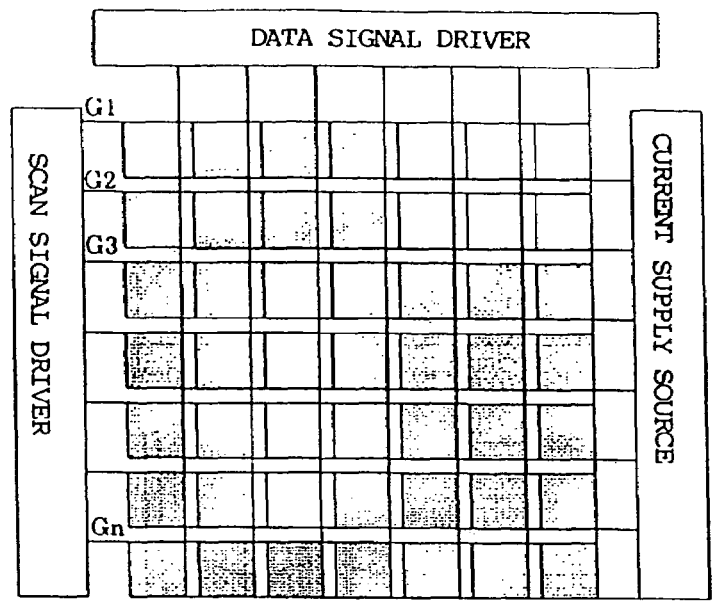
FIG. 2 schematically illustrates an example of a panel structure including an organic EL device and drive means.
Figure 3:
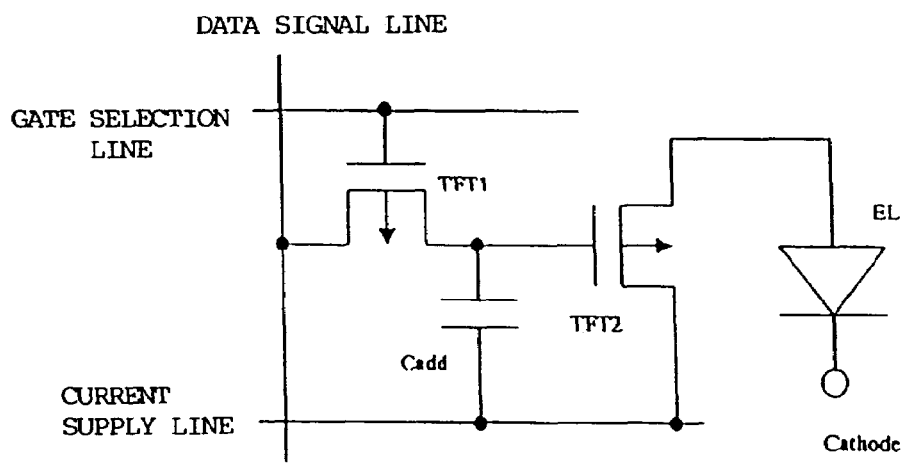
FIG. 3 illustrates an example of pixel circuit using TFTs (thin film transistors).

FIG. 2 schematically illustrates an example of a panel structure provided with an organic EL device and drive means. In this example, the number of pixels was set to 128×128 pixels. Incidentally, one pixel was composed of three color pixels comprising a green pixel, a blue pixel and a red pixel.

On a glass substrate, a thin film transistor circuit using polysilicon (referred to as a TFT circuit) was formed by a known method.

In regions corresponding to the respective color pixels, organic layers and a metal electrode layer were formed in the following thicknesses by vacuum deposition with a hand mask, followed by patterning. Organic layer structures corresponding to the respective color pixels are shown below.

Green pixel=α-NPD (40 nm)/CBP:phosphorescent material (=93:7 by weight) (30 nm)/BCP (20 nm)/Alq (40 nm)
Blue pixel: α-NPD (50 nm)/BCP (20 nm)/Alq (50 nm)
Red pixel: α-NPD (40 nm)/CBP:PtOEP (=93:7 by weight) (30 nm)/BCP (20 nm)/Alq (40 nm)

A luminescence layer for the green pixel was formed by co-deposition of CBP as a host material with a phosphorescent material (Example Compound No. 1) having a weight proportion of 7 wt. %.

In the panel shown in FIG. 2, a scanning signal driver, a data signal driver and a current supply source are disposed and are connected to gate selection lines, data signal lines and current supply lines, respectively. At intersections of the gate selection lines and data signal lines, a pixel circuit (equivalent circuit) shown in FIG. 3 is disposed, the gate selection lines G1, G2, G3 . . . Gn are sequentially selected by the scanning signal driver and in synchronism therewith, image (picture) signals are applied from the data signal driver.

Next, a pixel circuit operation is described with reference to the equivalent circuit shown in FIG. 3. When a selection signal is applied to a gate selection line, TFT1 is turned on so that a display signal is supplied from a data signal line to a capacitor Cadd, thereby determining the gate potential of TFT2, whereby a current is supplied to an organic luminescence device (abbreviate as EL) disposed at each pixel through a current supply line depending on the gate potential of TFT2. The gate potential of TFT2 is held at Cadd during one frame period, so that the current continually flows from the current supply line to the EL device during the period. As a result, luminescence can be retained during one frame period.

As a result, it has been confirmed that it was possible to display a desired image data, thus resulting in stable display with good image quality.

In this example, as the application to display, the driving scheme using the TFT circuit of an active-matrix scheme was used. However, the switching device used in the present invention need not be particularly restricted, and can also be readily applicable to a single-crystal silicon substrate, an MIM (metal-insulator-metal) device, an a-Si (amorphous silicon)-type TFT circuit, etc.

INDUSTRIAL APPLICABILITY

As described above, a luminescence device using a metal coordination compound represented by the above-mentioned formula (1) as a luminescent material had a high phosphorescence efficiency and could retain high-luminance luminescence for a long period. Further, the metal coordination compound is an excellent material allowing control of emission wavelength, particularly shift to a shorter wavelength. Further, the luminescence device of the present invention is also excellent as a display device.

A high-efficiency luminescence device according to the present invention is applicable to a product requiring energy economization or a high luminance. As applied examples, a display apparatus, an illumination apparatus, a printer light source or a backlight for a liquid crystal display apparatus, etc. are considered. As for a display apparatus, it allows a flat panel display which provides a highly recognizable display at a low energy consumption and is light in weight. As a printer light source, the luminescence device of the present invention can be used-instead of a laser light source of a laser beam printer which is currently extensively used. Independently addressable devices are arranged in an array form to effect a desired exposure on a photosensitive drum thereby forming an image. The apparatus volume can be remarkably reduced by using the devices of the present invention.

The invention claimed is:
1. A metal coordination compound of a formula selected from the group consisting of formulas (126) to (140), (292) to (297), (361) to (365), (373), (374), (395) to (397) and (420) to (422) in which (a) formulas (126) to (140) are:

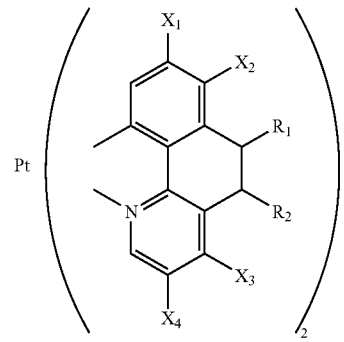

wherein

| No. | R1  | R2 | X1  | X2  | X3  | X4  | R7 | R8 | R9  | R10 |
|-----|-----|----|-----|-----|-----|-----|----|----|-----|-----|
| 126 | H   | H  | H   | H   | CF3 | H   | —  | —  | —   | —   |
| 127 | H   | H  | H   | H   | H   | CF3 | —  | —  | —   | —   |
| 128 | H   | H  | Ph3 | H   | H   | H   | —  | —  | —   | —   |
| 129 | H   | H  | Ph3 | H   | H   | CF3 | —  | —  | —   | —   |
| 130 | H   | H  | Ph2 | H   | H   | H   | H  | F  | H   | H   |
| 131 | H   | H  | Ph2 | H   | H   | H   | H  | H  | CF3 | H   |
| 132 | H   | H  | Tn5 | H   | H   | H   | H  | H  | —   | —   |
| 133 | H   | H  | Np3 | H   | H   | H   | H  | H  | —   | —   |
| 134 | H   | H  | H   | Tn5 | H   | H   | H  | H  | —   | —   |
| 135 | H   | H  | Tn7 | H   | H   | H   | H  | H  | —   | —   |
| 136 | CH3 | H  | F   | H   | H   | H   | —  | —  | —   | —   |
| 137 | CH3 | H  | CF3 | H   | H   | H   | —  | —  | —   | —   |
| 138 | CH3 | H  | H   | CF3 | H   | H   | —  | —  | —   | —   |
| 139 | CH3 | H  | F   | CF3 | H   | H   | —  | —  | —   | —   |
| 140 | CH3 | H  | H   | H   | H   | H   | —  | —  | —   | —   | and wherein

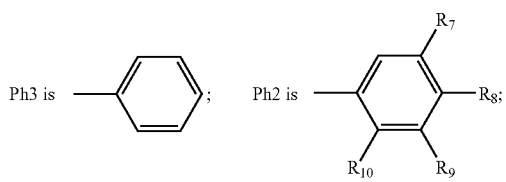

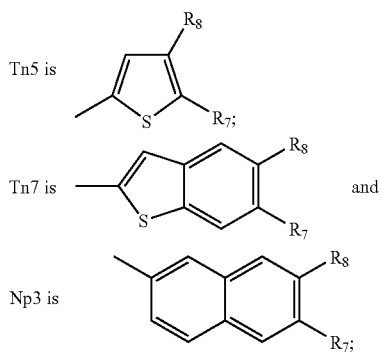

(b) formulas(292) to (297) are:
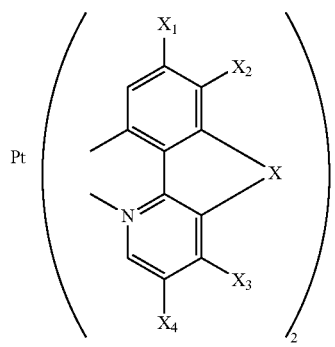
wherein
| No. | X | R1 | R2 | X1 | X2 | X3 | X4 |
|---|---|---|---|---|---|---|---|
| 292 | C | H | — | CF3 | H | H | H |
| 293 | O | H | H | H | CF3 | H | H |
| 294 | Z | — | — | F | CF3 | H | H |
| 295 | D' | H | — | CF3 | F | H | H |
| 296 | F' | — | — | Cl | CF3 | H | H |
| 297 | H' | — | — | OC4H9 | H | H | H; |
and wherein
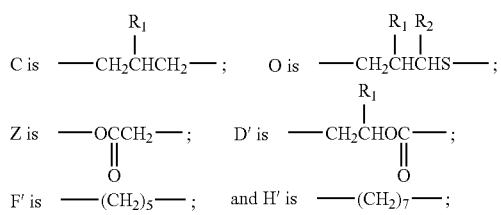
(c) formulas (361) to (365) are:
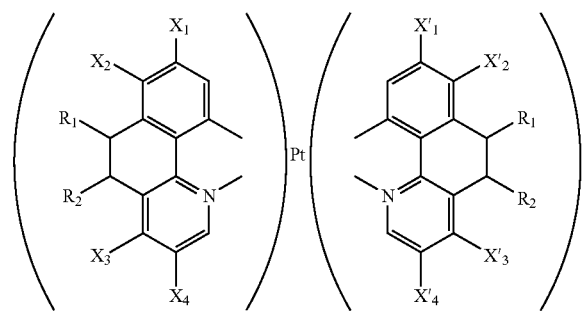
wherein
| No. | R1 | R2 | X1 | X2 | X3 | X4 | R7 | R8 | R9 | R10 |
|---|---|---|---|---|---|---|---|---|---|---|
|     | R1 | R2 | X1' | X2' | X3' | X4' | R7 | R8 | R9 | R10 |
| 361 | H | H | OC4H9 | H | H | H | — | — | — | — |
|     | H | H | H | OCH(CH3)2 | H | H | — | — | — | — |
| 362 | H | H | Br | H | H | H | — | — | — | — |
|     | H | H | H | H | Cl | H | — | — | — | — |
| 363 | H | H | H | H | H | Cl | — | — | — | — |
|     | H | H | H | H | CF3 | H | — | — | — | — |
| 364 | H | H | H | H | H | CF3 | — | — | — | — |
|     | H | H | Ph3 | H | H | H | — | — | — | — |
| 365 | H | H | Ph3 | H | H | CF3 | — | — | — | — |
|     | H | H | Ph2 | H | H | H | H | F | H | H; |
and wherein
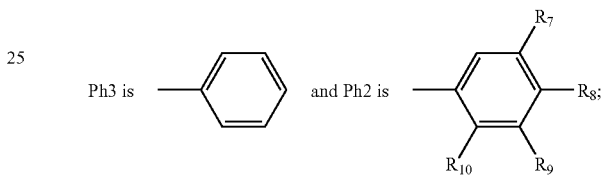
(d) formula (373) is:
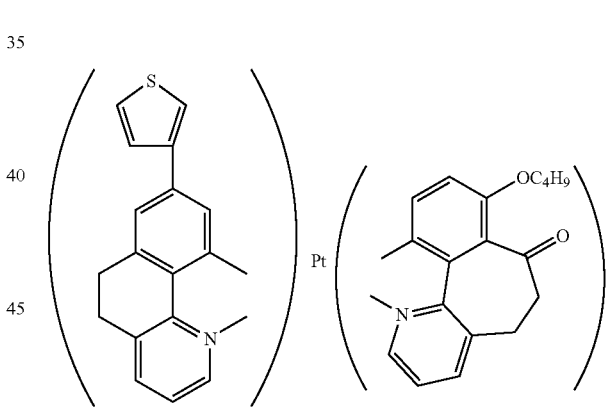
(e) formula (374) is
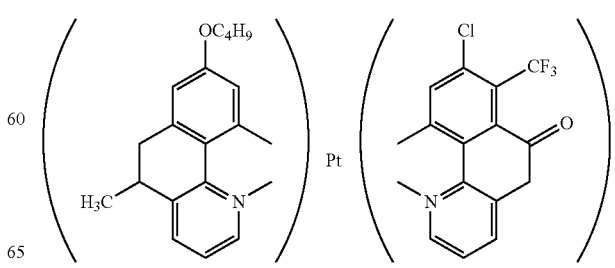

(f) formula 395 is

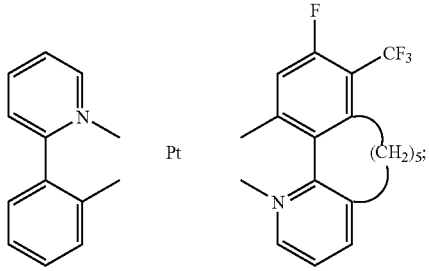

(g) formula 396 is

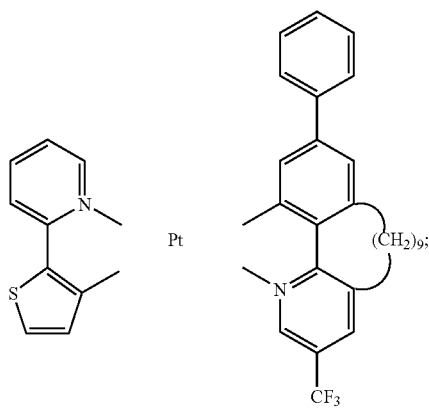

(h) formula 397 is

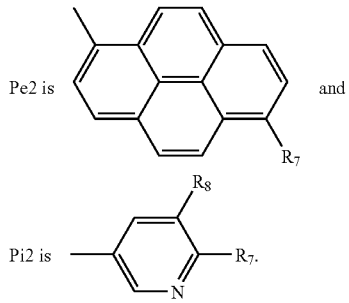

formulas (420) to (422) are:

[structure of Pt complex with X1, X2, X3, X4, E, G substituents]

wherein

| No | X<br>E<br>G | R1 | R2 | X1 | X2 | X3 | X4 | R7<br>R7<br>R7 | R8<br>R8<br>R8 | R9<br>E<br>R9<br>G<br>R9 | R10<br>R10<br>R10 |
|---|---|---|---|---|---|---|---|---|---|---|---|
| 420 | F'<br>CH3<br>CH3 | — | — | F | CF3 | H | H | —<br>—<br>— | —<br>—<br>— | —<br>—<br>— | —<br>—<br>— |
| 421 | J'<br>CF3<br>CF3 | — | — | Ph3 | H | H | CF3 | —<br>—<br>— | —<br>—<br>— | —<br>—<br>— | —<br>—<br>— |
| 422 | C<br>Pi2<br>Pi2 | H | — | Pe2 | H | H | H | H<br>H<br>H | —<br>H<br>H | —<br>—<br>— | —<br>—<br>— | and wherein F', C and PH3 are as above;

J' is —(CH2)9—,

Pe2 is [pyrenyl group with R7] and

Pi2 is [pyridyl group with R7, R8].

2. An electroluminescence device comprising: a substrate, a pair of electrodes disposed on the substrate and at least one species of a metal coordination compound according to claim 1.

* * * * *

UNITED STATES PATENT AND TRADEMARK OFFICE
CERTIFICATE OF CORRECTION

PATENT NO. : 7,078,115 B2
APPLICATION NO. : 10/942861
DATED : July 18, 2006
INVENTOR(S) : Takao Takiguchi et al.

It is certified that error appears in the above-identified patent and that said Letters Patent is hereby corrected as shown below:

COLUMN 5:

Line 61, "and B"," should read --and B"--.

COLUMN 8:

Line 30, "EL, device" should read --EL device--.

COLUMN 10:

Lines 35-48, " 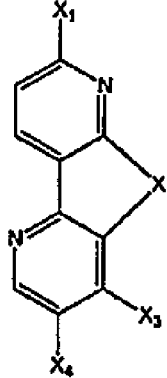 " should read -- 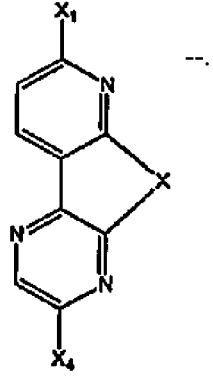 --.

COLUMN 11:

Line 20, "l$_9$" should read --L$_9$--; and

Lines 52-65, " 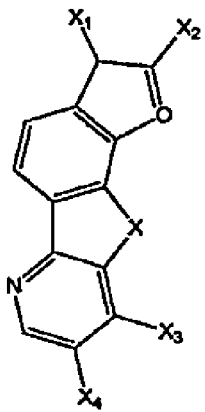 " should read -- 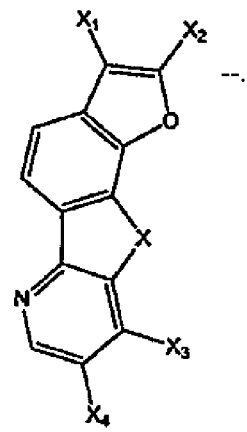 --.

UNITED STATES PATENT AND TRADEMARK OFFICE
CERTIFICATE OF CORRECTION

PATENT NO. : 7,078,115 B2  Page 2 of 6
APPLICATION NO. : 10/942861
DATED : July 18, 2006
INVENTOR(S) : Takao Takiguchi et al.

It is certified that error appears in the above-identified patent and that said Letters Patent is hereby corrected as shown below:

COLUMN 12:

Lines 42-53, " 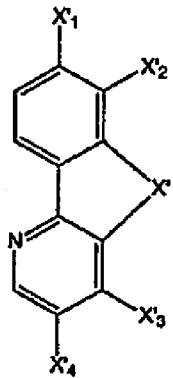 " should read -- 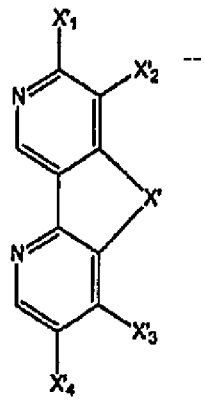 --

COLUMN 14:

Lines 17-30, " 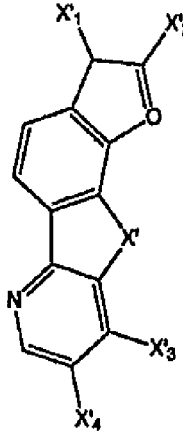 " should read -- 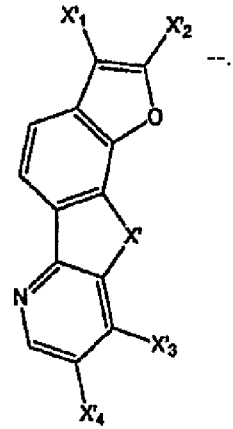 --.

COLUMN 15:

Line 33, "Pt:" should read --Pi:--.

UNITED STATES PATENT AND TRADEMARK OFFICE
CERTIFICATE OF CORRECTION

PATENT NO. : 7,078,115 B2  Page 3 of 6
APPLICATION NO. : 10/942861
DATED : July 18, 2006
INVENTOR(S) : Takao Takiguchi et al.

It is certified that error appears in the above-identified patent and that said Letters Patent is hereby corrected as shown below:

COLUMN 16:

Lines 15-27, " 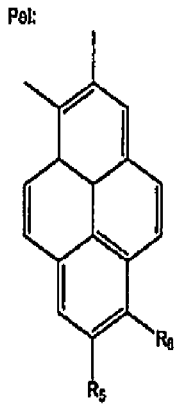 " should read -- 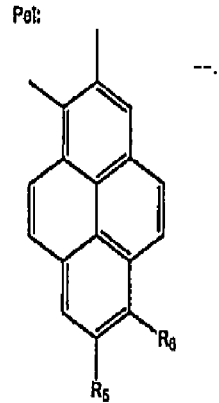 --.

COLUMN 31:

Table 1-10, "  385   Ir   2   1   L1   C   H   —  "
                                   —   Ph1   Pi should read --   385   Ir   2   1   L1   C   H   — --.
                                   —   Tn4   Pi

COLUMN 35:

Table 1-13, "  424   Pd   1   1   L1   B   H   H   H   OCH9CH3)2   H   H  "
                                                          CF3
                                                          CF3 should read -- 424   Pd   1   1   L1   B   H   H   H   OCH9(CH3)2   H   H --.
                                                          CF3
                                                          CF3

UNITED STATES PATENT AND TRADEMARK OFFICE
CERTIFICATE OF CORRECTION

PATENT NO. : 7,078,115 B2  Page 4 of 6
APPLICATION NO. : 10/942861
DATED : July 18, 2006
INVENTOR(S) : Takao Takiguchi et al.

It is certified that error appears in the above-identified patent and that said Letters Patent is hereby corrected as shown below:

COLUMN 39:

Lines 12-29, " 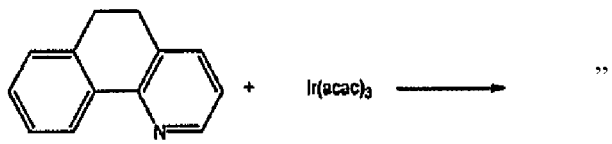 "

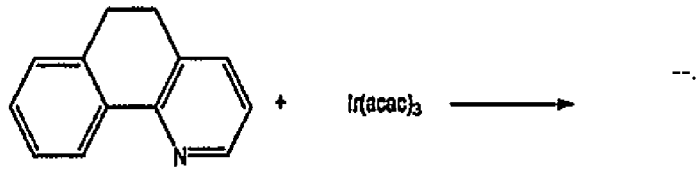

should read -- 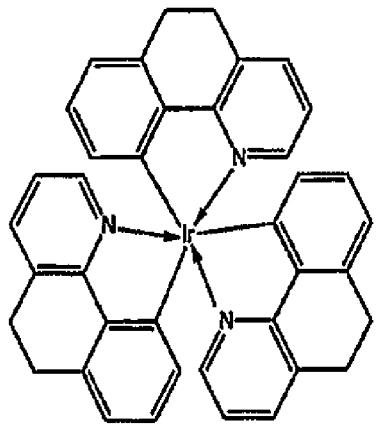 --.

UNITED STATES PATENT AND TRADEMARK OFFICE
CERTIFICATE OF CORRECTION

PATENT NO. : 7,078,115 B2  Page 5 of 6
APPLICATION NO. : 10/942861
DATED : July 18, 2006
INVENTOR(S) : Takao Takiguchi et al.

It is certified that error appears in the above-identified patent and that said Letters Patent is hereby corrected as shown below:

COLUMN 43:

Line 55, "used-instead" should read --used instead--.

COLUMN 46:

Lines 55-65,

"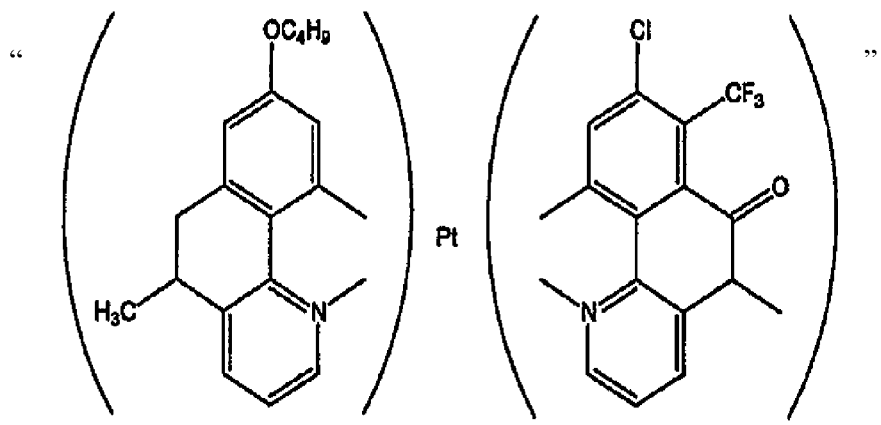"

should read

--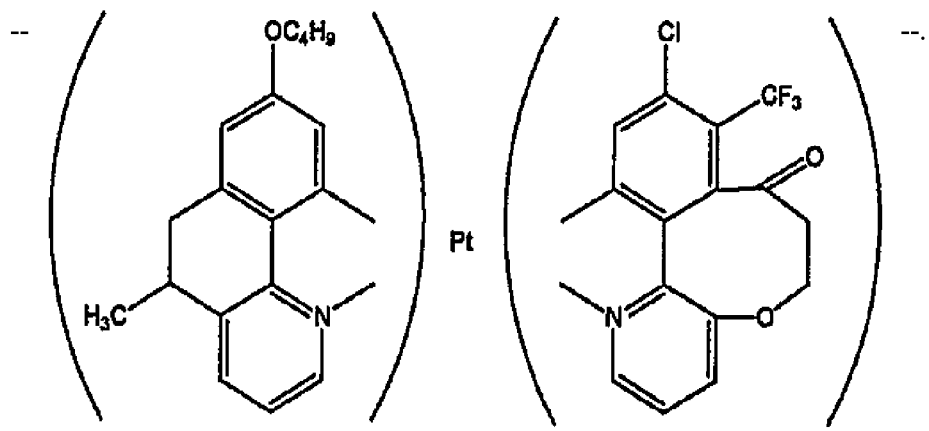--.

UNITED STATES PATENT AND TRADEMARK OFFICE
CERTIFICATE OF CORRECTION

PATENT NO. : 7,078,115 B2
APPLICATION NO. : 10/942861
DATED : July 18, 2006
INVENTOR(S) : Takao Takiguchi et al.

It is certified that error appears in the above-identified patent and that said Letters Patent is hereby corrected as shown below:

COLUMN 48:

Line 44, "and PH3" should read --and Ph3--.

Signed and Sealed this

Tenth Day of April, 2007

JON W. DUDAS
*Director of the United States Patent and Trademark Office*